(12) United States Patent
Nakai et al.

(10) Patent No.: US 11,602,381 B2
(45) Date of Patent: Mar. 14, 2023

(54) SPINAL IMPLANT SYSTEM AND METHOD

(71) Applicant: WARSAW ORTHOPEDIC, INC., Warsaw, IN (US)

(72) Inventors: Kenjiro Nakai, Osaka (JP); Koji Sato, Nagoya (JP); Tetsuya Sumida, Osaka (JP)

(73) Assignee: Medtronic Sofamor Danek, Co., Ltd., Osaka (JP)

( * ) Notice: Subject to any disclaimer, the term of this patent is extended or adjusted under 35 U.S.C. 154(b) by 0 days.

(21) Appl. No.: 17/268,868

(22) PCT Filed: Aug. 16, 2018

(86) PCT No.: PCT/JP2018/031057
§ 371 (c)(1),
(2) Date: Feb. 16, 2021

(87) PCT Pub. No.: WO2020/035958
PCT Pub. Date: Feb. 20, 2020

(65) Prior Publication Data
US 2021/0298798 A1 Sep. 30, 2021

(51) Int. Cl.
*A61B 17/70* (2006.01)
*A61B 90/00* (2016.01)

(52) U.S. Cl.
CPC ...... *A61B 17/7085* (2013.01); *A61B 17/7052* (2013.01); *A61B 90/03* (2016.02); *A61B 90/06* (2016.02); *A61B 2090/037* (2016.02); *A61B 2090/061* (2016.02)

(58) Field of Classification Search
CPC .............. A61B 17/7049; A61B 17/705; A61B 17/7052; A61B 17/7056
See application file for complete search history.

(56) References Cited

U.S. PATENT DOCUMENTS

| | | | | |
|---|---|---|---|---|
| 5,676,665 A | * | 10/1997 | Bryan | A61B 17/7032 606/250 |
| 8,313,514 B2 | * | 11/2012 | Puno | A61B 17/7049 606/250 |
| 9,381,044 B2 | * | 7/2016 | Robinson | A61B 17/7055 |
| 9,603,634 B1 | * | 3/2017 | Frankel | A61B 17/7083 |
| 9,956,008 B2 | * | 5/2018 | Agarwal | A61B 17/7035 |

(Continued)

FOREIGN PATENT DOCUMENTS

| | | |
|---|---|---|
| JP | 2016539762 A | 12/2016 |
| WO | WO2014/074892 A1 | 5/2014 |

(Continued)

OTHER PUBLICATIONS

International Search Report for PCT/JP2018/031057 date of completion is Oct. 29, 2018 (2 pages).

(Continued)

*Primary Examiner* — Jan Christopher L Merene
(74) *Attorney, Agent, or Firm* — Sorell, Lenna & Schmidt, LLP

(57) ABSTRACT

A spinal construct comprises at least one member that defines a first implant cavity and a second implant cavity oriented transverse to the first implant cavity. The at least one member has a surface that includes a lock disposed with the first implant cavity. Systems, implants, surgical instruments and methods of use are disclosed.

20 Claims, 25 Drawing Sheets

(56) References Cited

U.S. PATENT DOCUMENTS

| | | | |
|---|---|---|---|
| 10,499,954 B2* | 12/2019 | Unger | A61B 17/7047 |
| 10,624,679 B2* | 4/2020 | Murray | A61B 17/7007 |
| 2003/0130659 A1* | 7/2003 | Haider | A61B 17/7032 |
| | | | 606/302 |
| 2007/0083201 A1* | 4/2007 | Jones | A61B 17/7049 |
| | | | 606/252 |
| 2007/0173831 A1 | 7/2007 | Abdou | |
| 2007/0213723 A1 | 9/2007 | Markworth et al. | |
| 2007/0225712 A1* | 9/2007 | Altarac | A61B 17/7005 |
| | | | 606/64 |
| 2012/0253397 A1 | 10/2012 | Kraus | |
| 2014/0277145 A1 | 9/2014 | Reitblat et al. | |
| 2015/0112391 A1* | 4/2015 | Legallois | A61B 17/7056 |
| | | | 606/276 |
| 2016/0058478 A1* | 3/2016 | Agarwal | A61B 17/7035 |
| | | | 606/270 |
| 2016/0143665 A1 | 5/2016 | Biedermann et al. | |
| 2017/0258497 A1* | 9/2017 | Unger | A61B 17/7032 |
| 2017/0281237 A1* | 10/2017 | Murray | A61B 17/705 |
| 2017/0281247 A1 | 10/2017 | Murray et al. | |
| 2018/0132909 A1* | 5/2018 | Hackathorn, II | A61B 17/7065 |
| 2018/0344359 A1* | 12/2018 | Fiechter | A61B 17/7049 |
| 2020/0100816 A1* | 4/2020 | Mundis, Jr. | A61B 17/7052 |
| 2021/0161563 A1* | 6/2021 | Ebara | A61B 17/7056 |

FOREIGN PATENT DOCUMENTS

| | | |
|---|---|---|
| WO | 2014151037 A1 | 9/2014 |
| WO | WO2014/151037 A1 | 9/2014 |
| WO | 2017093853 A1 | 6/2017 |
| WO | WO2017/141459 A1 | 8/2017 |

OTHER PUBLICATIONS

European Patent Office 80298 Munich Germany, Extended European Search Report, Application No./Patent No. 18929944.9 dated Mar. 29, 2022.

Japanese Patent Office (JPO), Office Action dated Aug. 2, 2022 Japanese Patent Appln. No. 2021-506003.

* cited by examiner

SPINAL IMPLANT SYSTEM AND METHOD

TECHNICAL FIELD

The present disclosure generally relates to surgical implants for the treatment of spinal disorders, and more particularly to a surgical system and method for treatment of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods, connectors and plates can be used to provide stability to a treated region. During surgical treatment, one or more rods may be attached via fasteners to the exterior of two or more vertebral members to provide stability to a treated region. This disclosure describes an improvement over these prior technologies.

SUMMARY

In one embodiment, a spinal construct is provided. The spinal construct comprises at least one member that defines a first implant cavity and a second implant cavity oriented transverse to the first implant cavity. The at least one member has a surface that includes a lock disposed with the first implant cavity. In some embodiments, systems, implants, surgical instruments and methods are provided.

In one embodiment, the spinal construct comprises at least one connector including a hook that defines a first implant cavity and spaced apart arms that define the second implant cavity. Each of the arms include a provisional lock engageable with an existing spinal rod disposable with the first implant cavity.

In one embodiment, a method of treating a spine is provided. The method comprises the steps of: connecting a lateral member that defines a first cavity and a second cavity oriented transverse to the first cavity to a lateral existing rod implant such that a lock of the lateral member engages the lateral rod to provisionally fix the lateral rod with the first cavity; connecting an implant support with the lateral member; connecting a contra-lateral member that defines a first cavity and a second cavity oriented transverse to the first cavity of the contra-lateral member to an existing contra-lateral rod implant such that a lock of the contra-lateral member engages the contra-lateral rod to provisionally fix the contra-lateral rod with the first cavity of the contra-lateral member; and connecting an implant support with the contra-lateral member. Other embodiments may include lateral members where the orientation of the first cavity and the second cavity are variable or set at any angle relative to each other. The pair of lateral members may also be facing toward each other, facing away from each other, or in line with each other.

BRIEF DESCRIPTION OF THE DRAWINGS

The present disclosure will become more readily apparent from the specific description accompanied by the following drawings, in which.

DETAILED DESCRIPTION

Figure 1:
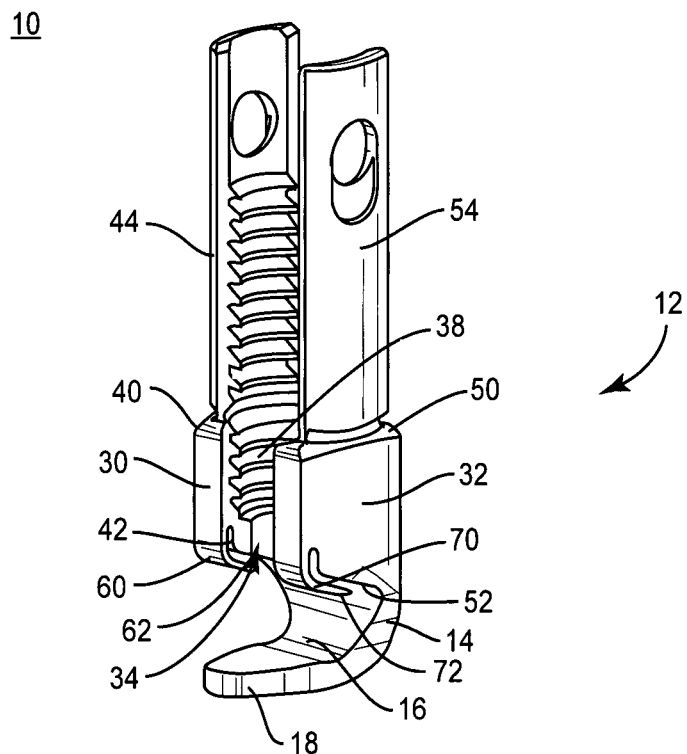
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system comprises a spinal construct including a connector and a cross-link spinal rod configured for percutaneous insertion. In some embodiments, the connector includes a hook portion configured for engagement with a lateral and/or a contra-lateral spinal rod. In some embodiments, the connector includes a tab extender configured to facilitate percutaneous insertion. In some embodiments, the connector includes a temporary locking mechanism, such as, for example, a provisional locking element to facilitate connection with a lateral and/or a contra-lateral spinal rod. In some embodiments, the surgical system includes a lateral connector and a contra-lateral connector to fix a cross-link spinal rod with a lateral and a contra-lateral spinal rod.

In some embodiments, the present surgical system is employed with a method of use that includes the step of connecting tab extenders with a connector. In some embodiments, the surgical system is employed with a method of use that includes the step of percutaneously delivering the connector along a surgical pathway for connection with a lateral and/or a contra-lateral spinal rod. In some embodiments, a hook portion of the connector is engaged with a lateral and/or a contra-lateral spinal rod. In some embodiments, the connector is provisionally fixed with a lateral and/or a contra-lateral spinal rod. In some embodiments, the surgical system is employed with a method of use that includes the step of engaging a measuring device, such as, for example, a caliper or a ruler with tab extenders to determine a length of a cross-link spinal rod by measuring a distance between a lateral and/or a contra-lateral spinal rod.

In some embodiments, the present surgical system is employed with a method of use that includes the step of inserting a dilator via a lateral approach to provide a passageway for insertion of a cross-link spinal rod. In some embodiments, a trocar and/or a chisel are engaged with a dilator to cut and/or disrupt tissue surfaces of vertebrae for passage of the cross-link spinal rod. In some embodiments, the trocar and/or chisel are configured to cut and/or disrupt tissue to clear a passageway through tissue, such as, for example, a spinous process and/or a supraspinatus ligament.

In some embodiments, the present surgical system is employed with a method of use that includes the step of engaging a rod inserter with a cross-link spinal rod to direct and/or guide the cross-link spinal rod into engagement with the connectors. In some embodiments, the cross-link spinal rod is rotated, for example, 180 degrees. In some embodiments, the surgical system is employed with a method of use that includes the step of engaging a driver to a set screw with connectors to fix the cross-link spinal rod with the connectors. In some embodiments, an instrument is engaged with the connectors to break off tabs from the connectors.

In some embodiments, the present surgical system includes a spinal construct that is employed with methods of connection to a multi-axial screw and rod interconnection. In some embodiments, the interconnection is within the rod slot or rod accepting feature of a multi-axial screw, hook, or other bony attachment anchor and can be below or on top of the rod, or around a set screw or locking member of the interconnection. In some embodiments, the spinal construct has a low profile and axial size configuration of the connection, which reduces the size of the spinal construct while providing versatility in connection. In some embodiments, the spinal construct reduces stress on a rod construct by removing an extra point of fixation on the segmental construct because the interconnection is within an existing interconnection. In some embodiments, this connection is useful when crosslinking and extending from a construct, and/or for screw extension connectors.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 may be employed, for example, with minimally invasive procedures, including percutaneous techniques, mini-open surgical techniques and/or open surgical techniques to deliver and introduce instrumentation and/or implants, such as, for example, a spinal construct, at a surgical site within a subject body of a patient, which includes, for example, a spine having vertebrae V, as shown, for example, in FIGS. 6-31. In some embodiments, the spinal constructs can include one or more bone fasteners, spinal rods, connectors and/or plates.

Figure 6:
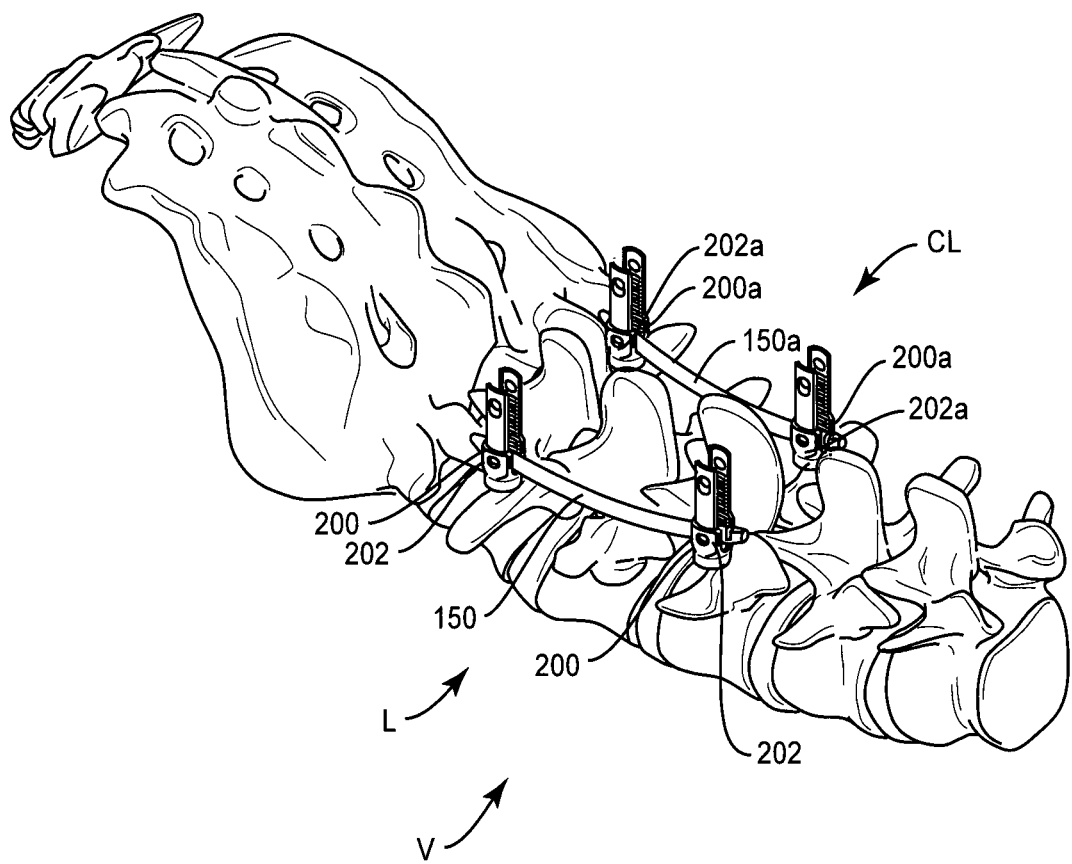
FIG. 6 is a perspective view of components of one embodiment of a system in accordance with the principles of the present disclosure disposed with vertebrae.

Spinal implant system 10 includes a spinal construct 11 comprising a member, such as, for example, a connector 12. Spinal implant system 10 includes a lateral connector 12 engageable with a lateral spinal rod 150 and a contra-lateral connector 12a, similar to connector 12 described herein, which is engageable with a contra-lateral spinal rod 150a (FIG. 6). A transverse spinal rod 152 is configured to connect connectors 12, 12a and link lateral spinal rod 150 and contra-lateral spinal rod 150a, as described herein. In some embodiments, spinal rod 152 reduces stress on one or more components of the spinal construct including spinal rods 150, 150a by removing one or more points of fixation with vertebrae V because the interconnection of spinal rods 150, 150a with rod 152 is within an existing interconnection of spinal rods 150, 150a with vertebrae V. In some embodiments, the spinal construct can include one or a plurality of members.

Connector 12 includes a surface 14 that defines an implant cavity 16, as shown in FIG. 1. Surface 14 includes a protrusion, such as, for example, a hook 18 extending from surface 14. Hook 18 defines a passageway 20 configured to capture a spinal implant, such as, for example, spinal rod 150 within cavity 16. Passageway 20 extends along an axis A1. In some embodiments, cavity 16 may have various cross section configurations, such as, for example, oval, oblong, triangular, rectangular, square, polygonal, irregular, uniform, non-uniform, variable, tubular and/or tapered. In some embodiments, rod 150 is in co-axial or parallel alignment with axis A1 when rod 150 is disposed in cavity 16. In some embodiments, rod 150 is disposed transverse to axis A1 when rod 150 is disposed in cavity 16.

Figure 2:
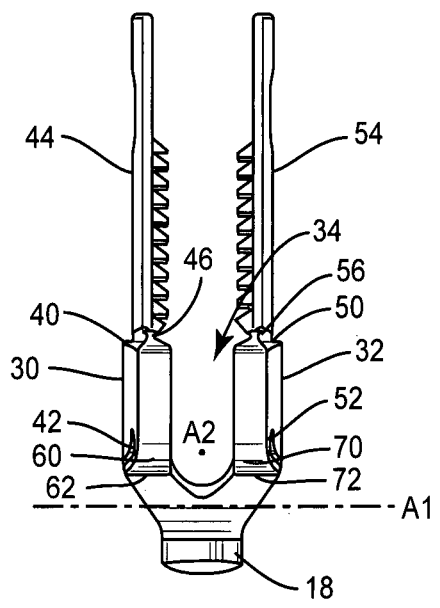
FIG. 2 is a side view of the components shown in FIG. 1.
Figure 3:
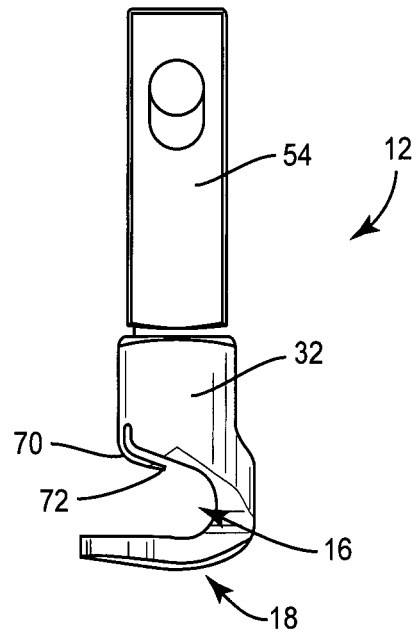
FIG. 3 is a side view of the components shown in FIG. 1.

Connector 12 includes a pair of spaced apart arms 30, 32. Arms 30, 32 define a U-shaped implant cavity 34 therebetween configured for disposal of a spinal implant, such as, for example, spinal rod 152. Cavity 34 extends along an axis A2 and extends transverse to axis A1, as shown in FIG. 2. In some embodiments, arm 30, arm 32 and/or cavity 34 may be disposed at alternate orientations, relative to axis A1, such as, for example, perpendicular and/or other angular orientations such as acute or obtuse, co-axial and/or may be offset or staggered. In some embodiments, cavity 34 may have various cross section configurations, such as, for example, oval, oblong, triangular, rectangular, square, polygonal, irregular, uniform, non-uniform, variable, tubular and/or tapered. In some embodiments, rod 152 is in co-axial or parallel alignment with axis A2 when rod 152 is disposed in cavity 34. In some embodiments, rod 152 is disposed transverse to axis A2 when rod 152 is disposed in cavity 34.

Figure 5:
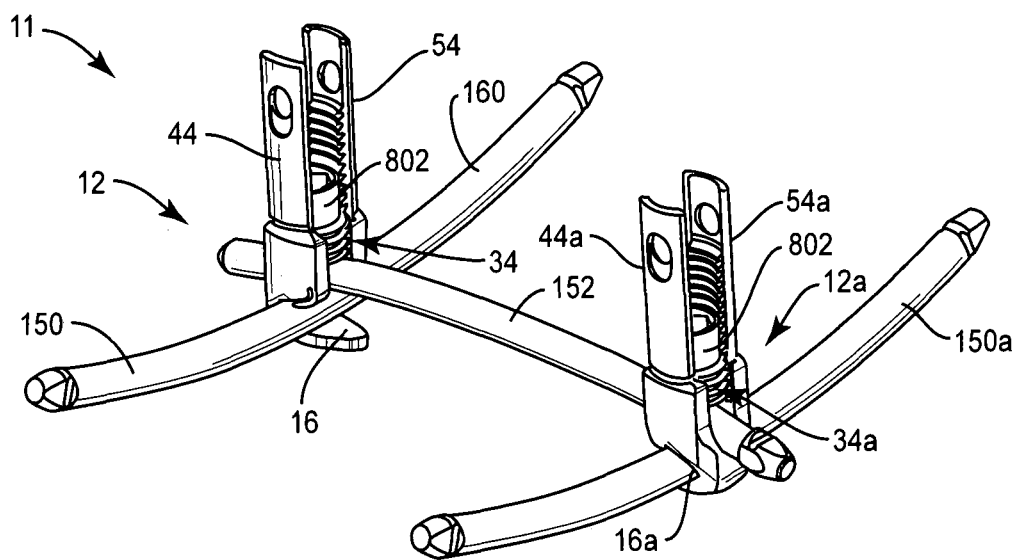
FIG. 5 is a perspective view of components of one embodiment of a system in accordance with the principles of the present disclosure.

Arms 30, 32 each include a thread form 38 configured for engagement with a coupling member, such as, for example, a setscrew 802 to retain spinal rod 152 within cavity 34, as shown in FIG. 5. In some embodiments, arms 30, 32 may be disposed with the coupling member in alternate fixation configurations, such as, for example, friction fit, pressure fit, locking protrusion/recess, locking keyway and/or adhesive.

Arm 30 extends between a surface 40 and a surface 42. Surface 40 includes a break away tab 44 that is frangibly connected to arm 30 at a portion 46. Portion 46 is fabricated from a fracturing and/or frangible material such that manipulation of tab 44 relative to arm 30 can fracture and separate tab 44 from arm 30 along portion 46 at a predetermined force and/or torque limit, as described herein. Arm 32 extends between a surface 50 and a surface 52. Surface 50 includes a break away tab 54 that is frangibly connected to arm 32 at a portion 56. Portion 56 is fabricated from a fracturing and/or frangible material such that manipulation of tab 54 relative to arm 32 can fracture and separate tab 54 from arm 32 along portion 56 at a predetermined force and/or torque limit, as described herein.

In some embodiments, as force and/or torque is applied to tab 44, and/or tab 54 and resistance increases, for example, the predetermined torque and force limit is approached. In some embodiments, tab 44 and/or tab 54 are configured to facilitate reduction of one or more spinal rods, as described herein, with a bone fastener and/or vertebrae. Tabs 44, 54 are configured to extend an overall height of bone connector 12 and facilitate disposal of one or more spinal rods with cavity 34. In some embodiments, tabs 44, 54 can fracture and separate at a predetermined force or torque limit, which may be in a range of approximately 2 Newton meters (N-m) to 8 Nm. In some embodiments, tabs 44, 54 and arms 30, 32 may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of tabs 44, 54 from arms 30, 32.

Surface 42 includes a lock, such as, for example, a spring tab 60 configured to provisionally lock spinal rod 150 with connector 12, as described herein. Tab 60 includes a surface, such as, for example, a tip 62 configured to deflect, snap and/or bias into engagement with spinal rod 150 to form a friction fit between a surface 160 of spinal rod 150 and tip 62. Tab 60 extends from surface 42 into cavity 16. Tab 60 is deflected inward upon engagement with spinal rod 150 such that the resultant bias forms a friction fit between surface 160 and tip 62.

Surface 52 includes a lock, such as, for example, a spring tab 70 configured to provisionally lock spinal rod 150 with connector 12, as described herein. Tab 70 includes a surface, such as, for example, a tip 72 configured to deflect, snap and/or bias into engagement with spinal rod 150 to form a friction fit between a surface 160 of spinal rod 150 and tip 72. Tab 70 extends from surface 52 into cavity 16. Tab 70 is deflected inward upon engagement with spinal rod 150 such that the resultant bias forms a friction fit between surface 160 and tip 72. Tabs 60, 70 provisionally lock connector 12 with spinal rod 150. Tabs 60, 70 temporarily fix connector 12 with spinal rod 150 to maintain a position of connector 12 during insertion and/or engagement of spinal rod 152 with cavity 34. After spinal rod 152 is disposed with cavity 34, set screw 802 is engaged with connector 12 to fix connector 12 with spinal rod 150.

Tabs 60, 70 are monolithically formed with connector 12. In some embodiments, tabs 60, 70 may have various lengths. In some embodiments, all or only a portion of tabs 60, 70 may have a semi-rigid, flexible or elastic configuration and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. In some embodiments, tabs 60, 70 provide a selective amount of flexion relative to spinal rod 150. In some embodiments, tabs 60, 70 may have a flexible configuration, which includes movement in an upwards and/or downwards direction. In some embodiments, tabs 60, 70 may be compressible. In some embodiments, tabs 60, 70 can include a plurality of separately attachable or connectable portions or sections, such as bands or loops, or may be monolithically formed as a single continuous element.

Figure 4:
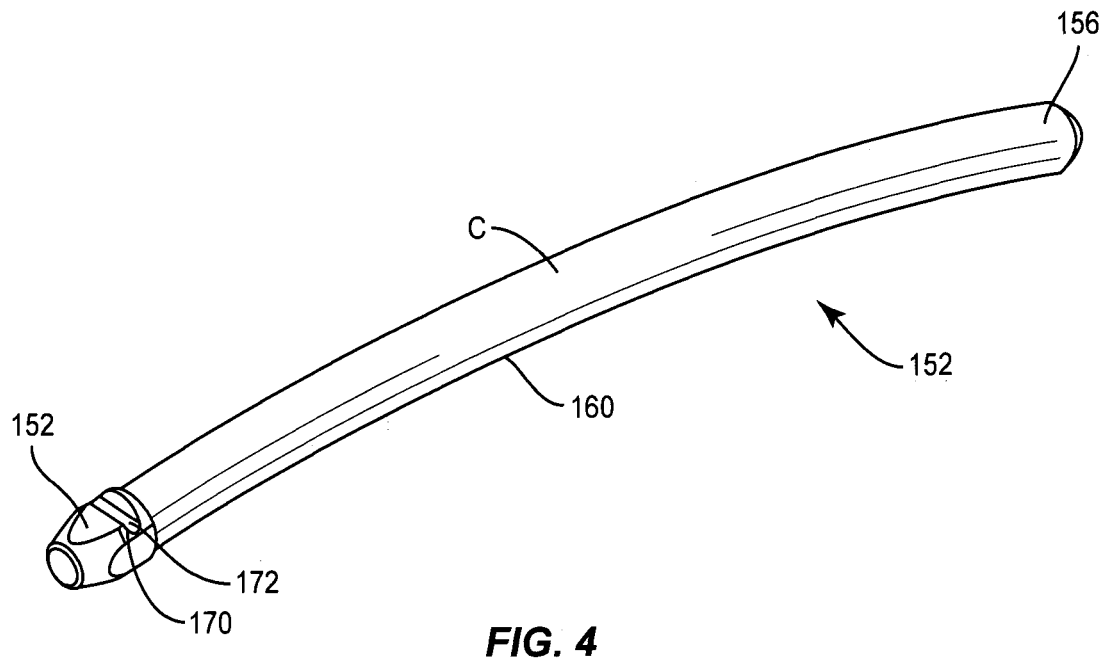
FIG. 4 is a perspective view of components of one embodiment of a system in accordance with the principles of the present disclosure.

Spinal rod 152 extends between an end 154 and an end 156, as shown in FIG. 4. End 154 includes a surface 170 that defines a groove 172. Groove 172 is configured to facilitate connection of a surgical instrument, such as, for example, a rod inserter 700, as described herein. Spinal rod 152 includes a curvature C. In some embodiments, spinal rod 152 may have various cross sectional configurations, such as, for example, circular, oval, oblong, rectangular, triangular, square, polygonal, irregular, uniform, non-uniform, variable, tubular and/or tapered. In some embodiments, the thickness defined by spinal rod 152 may be uniformly increasing or decreasing, or have alternate diameter dimensions along its length. In some embodiments, spinal rod 152 may have various cross section configurations, such as, for example, oval, oblong, triangular, rectangular, square, polygonal, irregular, uniform, non-uniform, variable and/or tapered. In some embodiments, spinal rod 152 may extend in various configurations, such as, for example, linear, arcuate, curved, angular and/or pre-bent according to a selected configuration of vertebrae.

In some embodiments, all or only a portion of spinal rod 152 may have a semi-rigid, flexible or elastic configuration and/or have elastic and/or flexible properties similar to the properties from materials, such as, for example, fabric, silicone, polyurethane, silicone-polyurethane, copolymers, rubbers, polyolefin rubber, elastomers, thermoplastic elastomers, thermoset elastomers and elastomeric composites. In some embodiments, spinal rod 152 can include a plurality of separately attachable or connectable portions or sections, such as bands or loops, or may be monolithically formed as a single continuous element.

In assembly, operation and use, spinal implant system 10, similar to the systems and methods described herein, is employed with a surgical procedure, as described herein, for treatment of a condition or injury of an affected section of the spine including vertebrae V, as shown in FIGS. 6-31.

In use, to treat the affected section of the spine, a medical practitioner obtains access to a surgical site including vertebrae V in any appropriate manner, such as through incision and retraction of tissues. Spinal implant system 10, including spinal construct 11 described herein, may be used in any existing surgical method or technique including open surgery, mini-open surgery, minimally invasive surgery and percutaneous surgical implantation, whereby vertebrae V are accessed through a micro-incision, or sleeve that provides a protected passageway to the area. Once access to the surgical site is obtained, the particular surgical procedure is performed for treating the spinal disorder. Spinal implant system 10 is then employed to augment the surgical treatment.

An incision is made in the body of a patient and a cutting instrument (not shown) creates a surgical pathway to access vertebrae V. The surgical pathway is utilized for implantation of components of spinal implant system 10. A preparation instrument (not shown) can be employed to prepare tissue surfaces of vertebrae V, as well as for aspiration and irrigation of a surgical region.

Bone fasteners 200 are engaged with vertebrae V along a lateral side L of vertebrae V, as show in FIG. 6. Spinal rod 150 is delivered along the surgical pathway to a surgical site adjacent vertebrae V. Spinal rod 150 is disposed with receivers 202 of bone fastener 200 along vertebrae V. In some embodiments, spinal implant system 10 includes a second set of bone fasteners 200a and spinal rod 150a delivered along the surgical pathway to the surgical site adjacent a contra-lateral side CL of vertebrae V. Spinal rod 150a is disposed with receivers 202a of bone fastener 200a along vertebrae V.

Bone fasteners 200 and bone fasteners 200a are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of spinal implant system 10 can be varied according to practitioner preference, patient anatomy or surgical procedure parameters.

Figure 7:
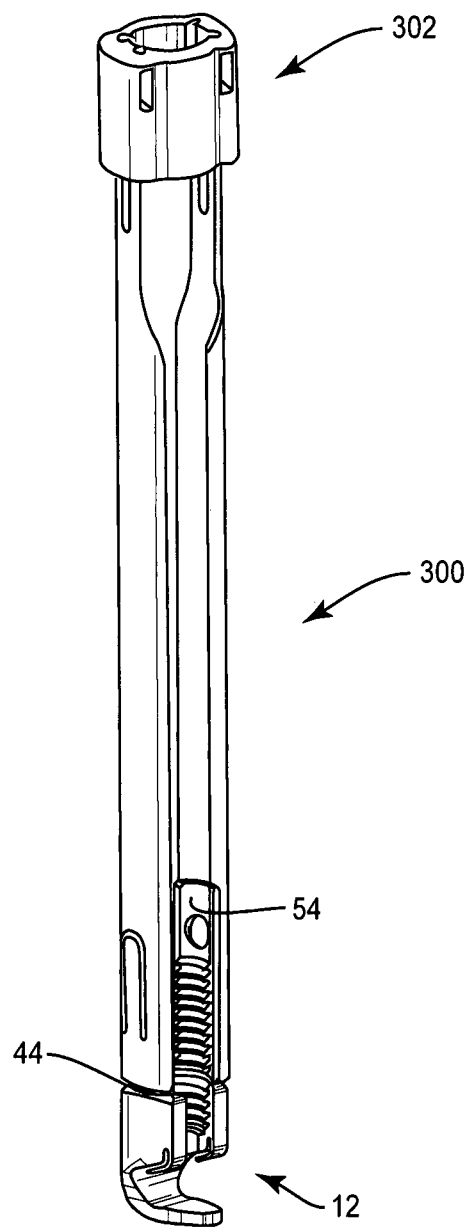
FIG. 7 is a perspective view of components of one embodiment of a system in accordance with the principles of the present disclosure.
Figure 8:
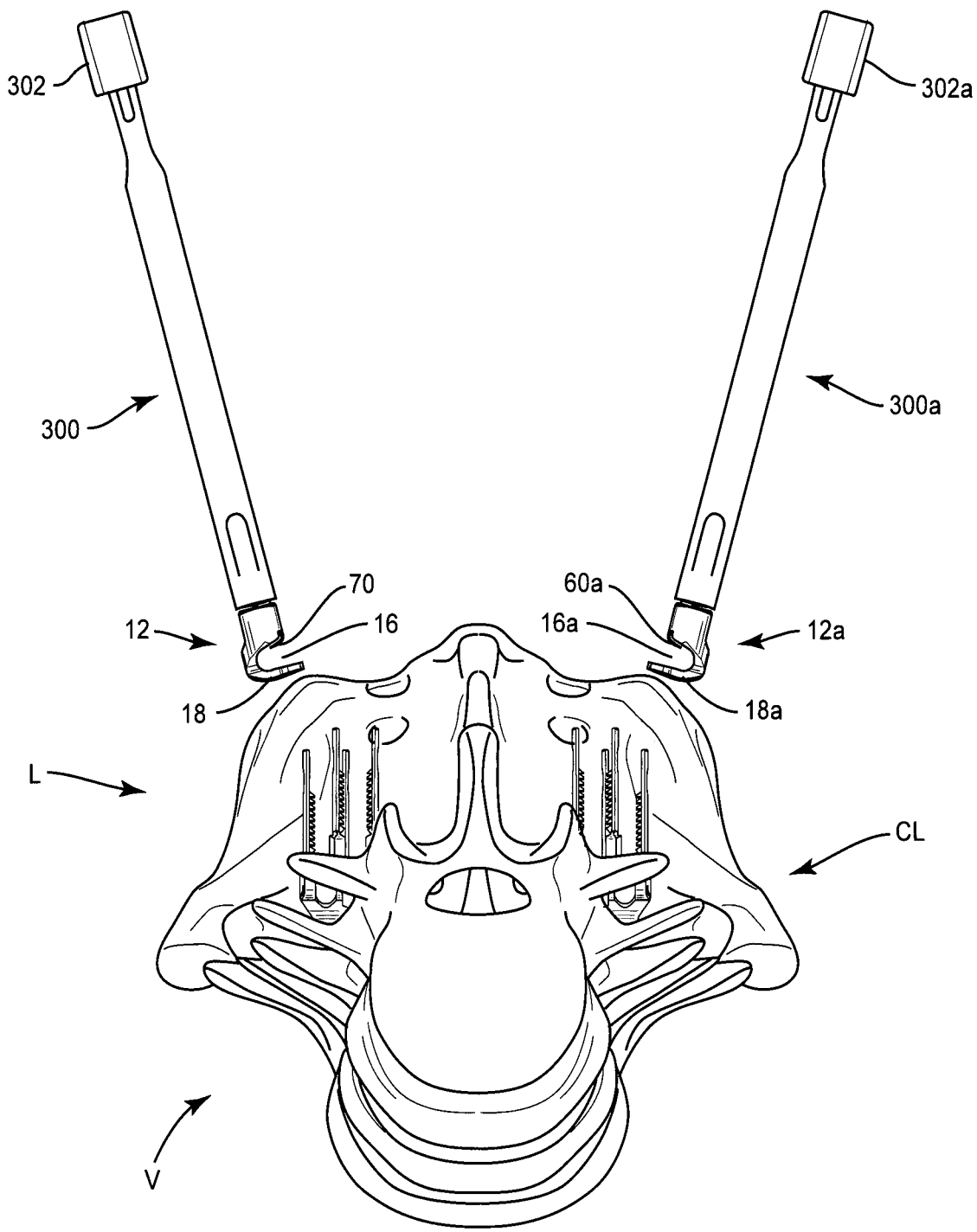
FIG. 8 is a plan view of components of one embodiment of a system in accordance with the principles of the present disclosure disposed with vertebrae.
Figure 9:
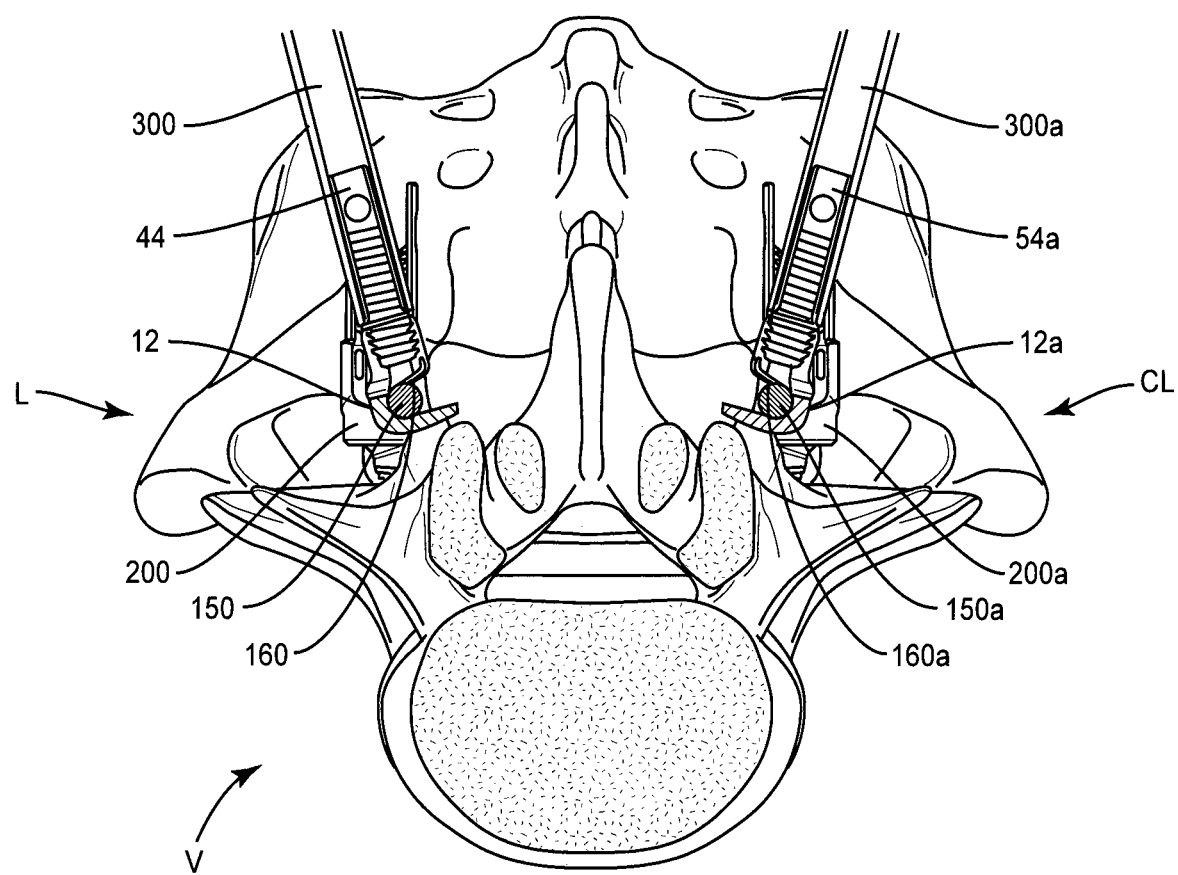
FIG. 9 is a plan view of components of one embodiment of a system in accordance with the principles of the present disclosure disposed with vertebrae.
Figure 10:
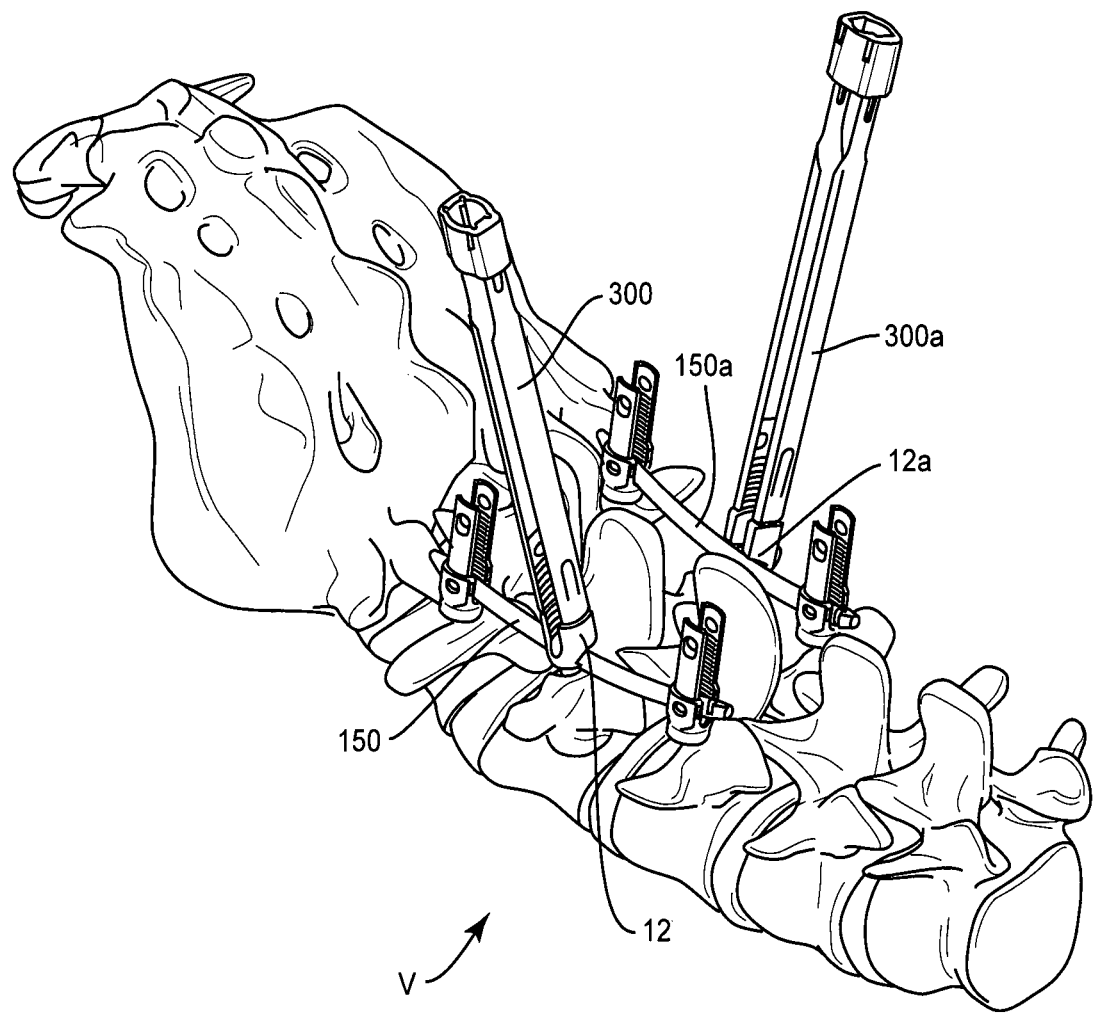
FIG. 10 is a perspective view of components of one embodiment of a system in accordance with the principles of the present disclosure disposed with vertebrae.

In some embodiments, tab extenders 300 are connected with tabs 44, 54, described herein. An extender cap 302 is engaged with tab extenders 300, as shown in FIG. 7. Connector 12 is delivered along the surgical pathway for connection with spinal rod 150, as shown in FIGS. 8-10. Spinal rod 150 is translated into cavity 16. Surface 160 compresses tabs 60, 70 such that spinal rod 150 is snap fit with hook 18. Tips 62, 72 form a friction fit between surface 160 and tips 60, 70 to provisionally fix spinal rod 150 with hook 16. The ruler 500 may also be used under fluoroscopy, X-ray or similar imaging techniques to determine a length of rod 152.

Tab extenders 300a are connected with tabs 44a, 54a, as shown in FIG. 9. An extender cap 302a is engaged with tab extenders 300a. Connector 12a is delivered along the surgical pathway for connection with spinal rod 150a. Spinal rod 150a is translated into cavity 16a of connector 12a, similar to the components of connector 12 described herein. Surface 160a compresses tabs 60a, 70a such that spinal rod 150a is snap fit with hook 18a. Tips 62a, 72a form a friction fit between surface 160a and tips 60a, 70a to provisionally fix spinal rod 150a with hook 16a.

Figure 11:
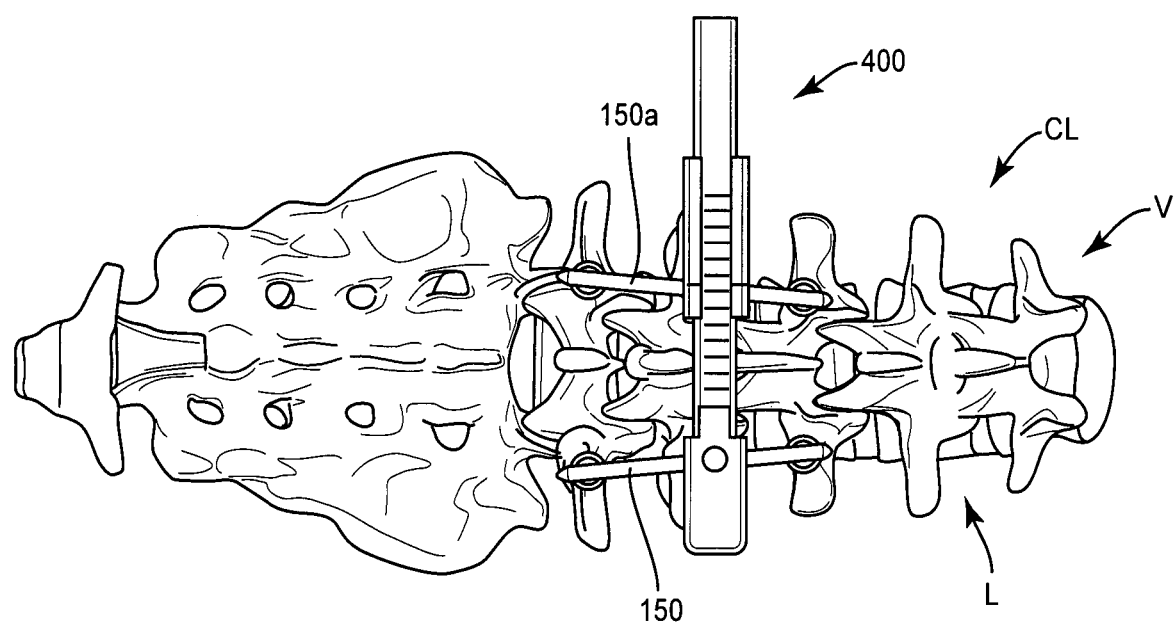
FIG. 11 is a plan view of components of one embodiment of a system in accordance with the principles of the present disclosure disposed with vertebrae.
Figure 12:
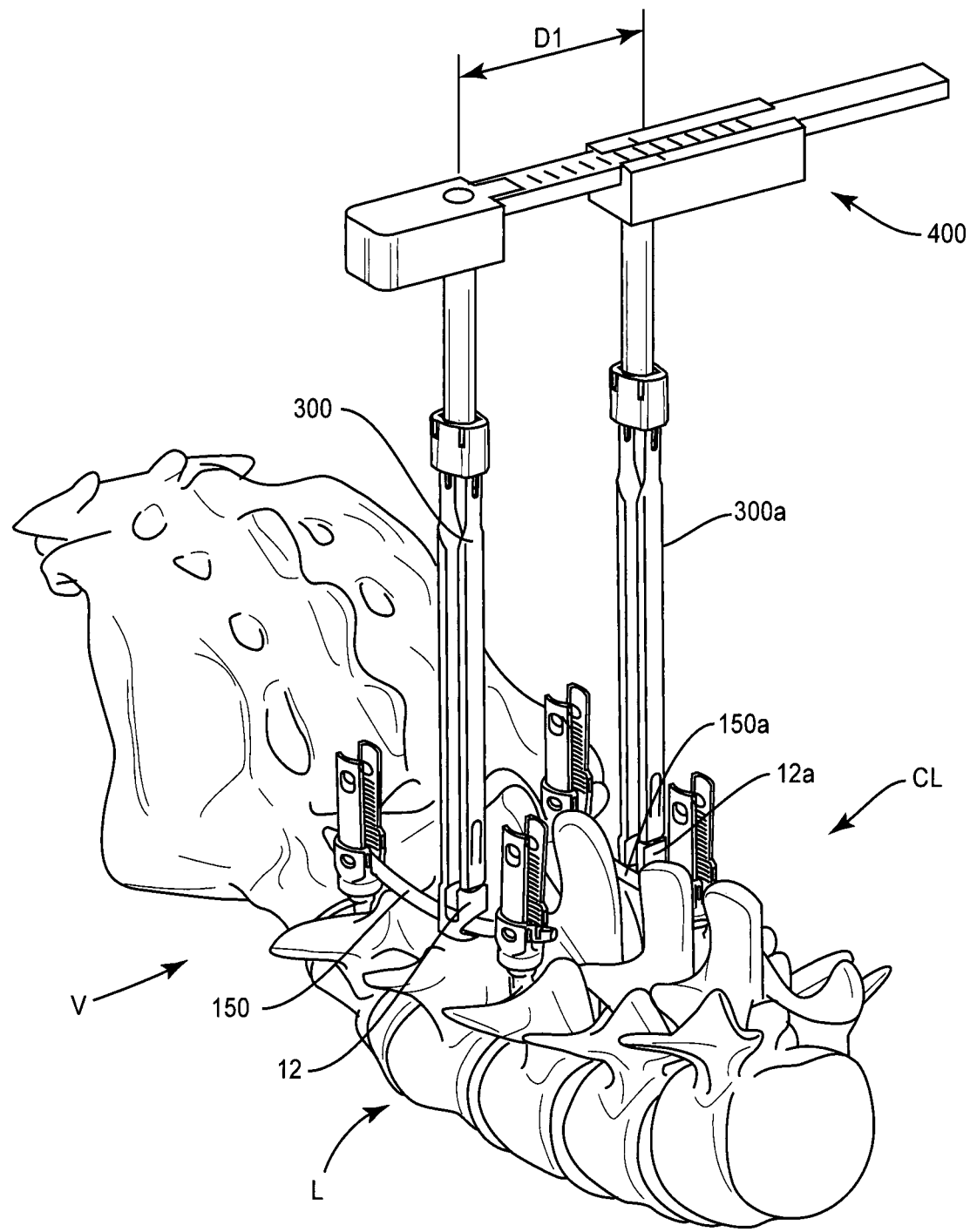
FIG. 12 is a perspective view of the components and vertebrae shown in FIG. 11.
Figure 13:
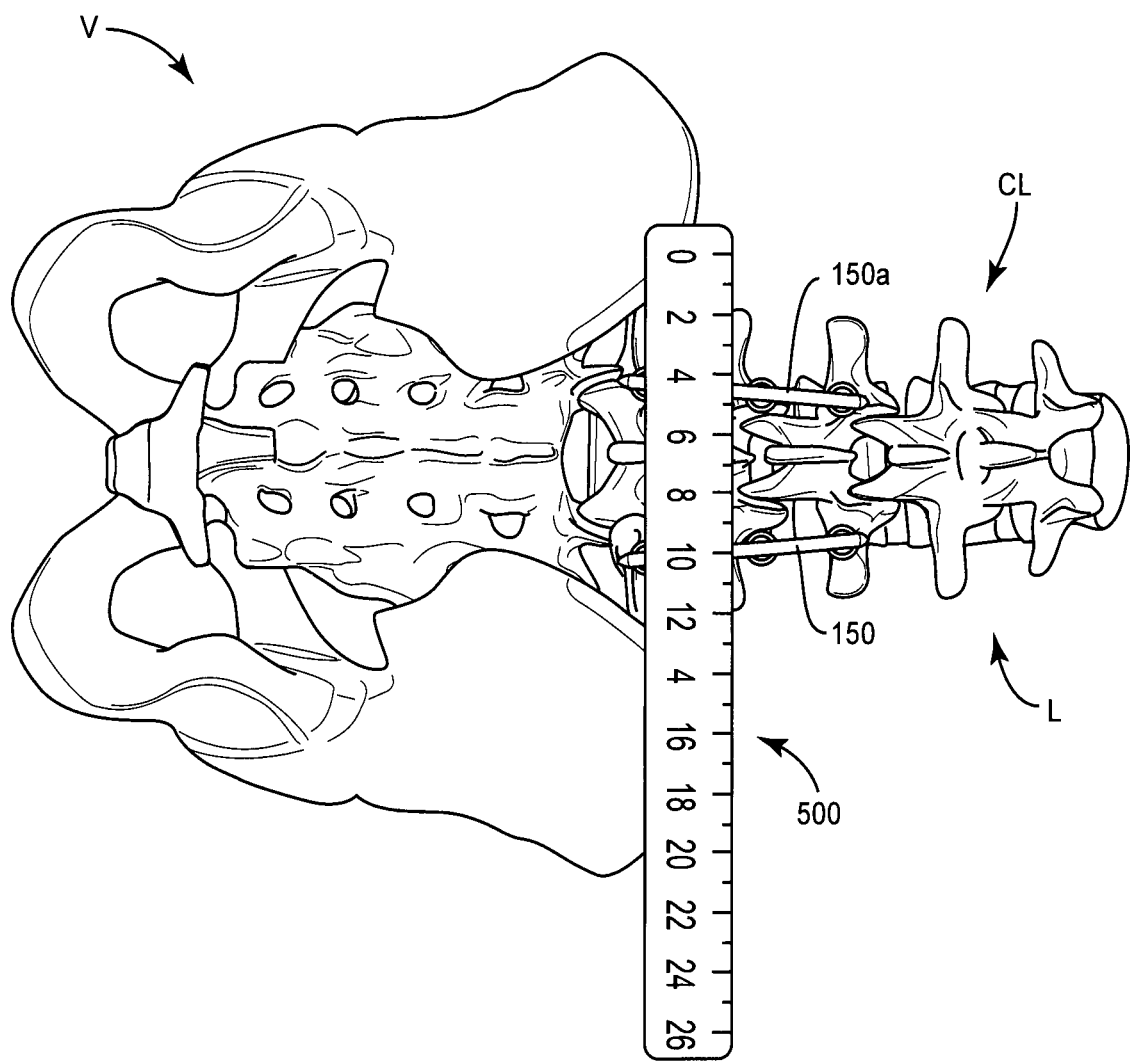
FIG. 13 is a plan view of components of one embodiment of a system in accordance with the principles of the present disclosure disposed with vertebrae.
Figure 14:
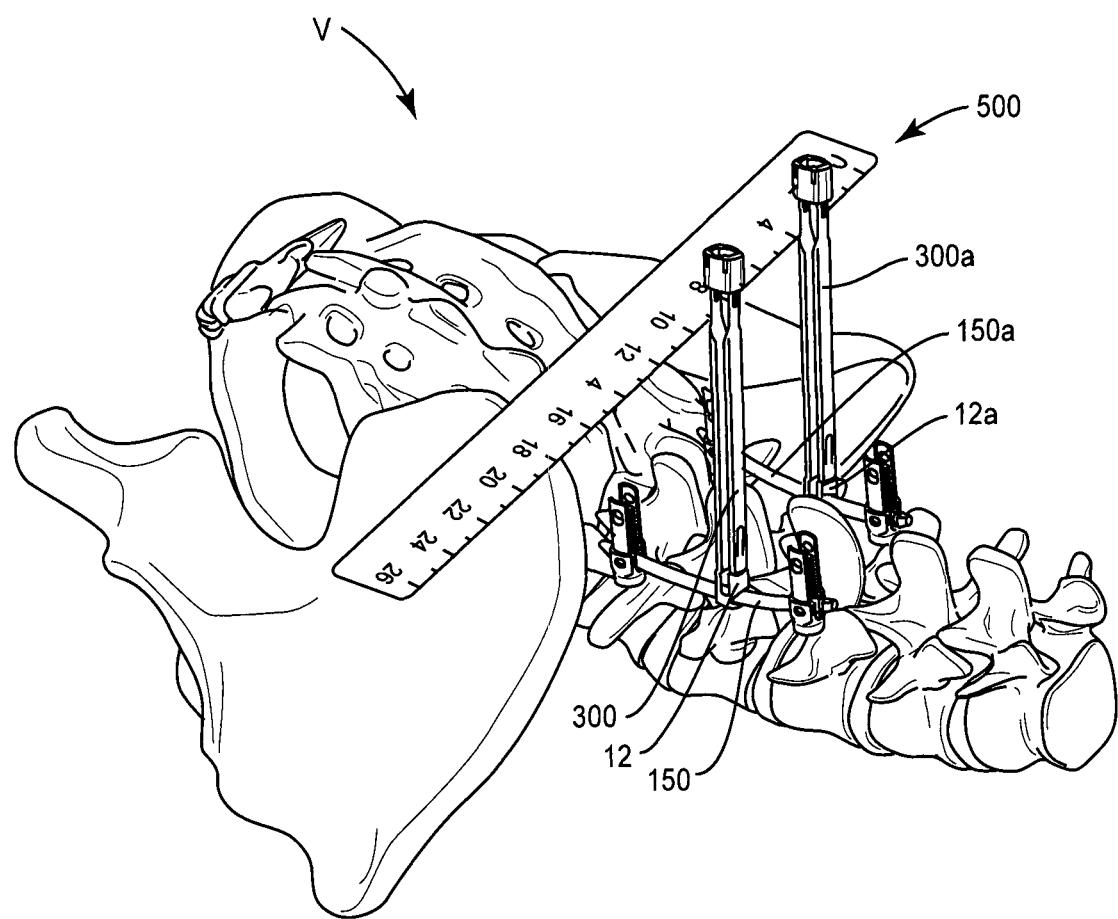
FIG. 14 is a perspective view of the components and vertebrae shown in FIG. 13.

In some embodiments, a measuring device, such as, for example, a caliper 400 is utilized to determine a length of spinal rod 152, as shown in FIGS. 11 and 12. Caliper 400 is engaged with tab extenders 300, 300a such that a distance D1 between connectors 12, 12a can be determined, as shown in FIG. 12. Determining distance D1 provides a length of rod 152 to link rods 150, 150a via connectors 12, 12a. In some embodiments, a ruler 500 is utilized to determine a length of spinal rod 152, as shown in FIGS. 13 and 14.

Figure 15:
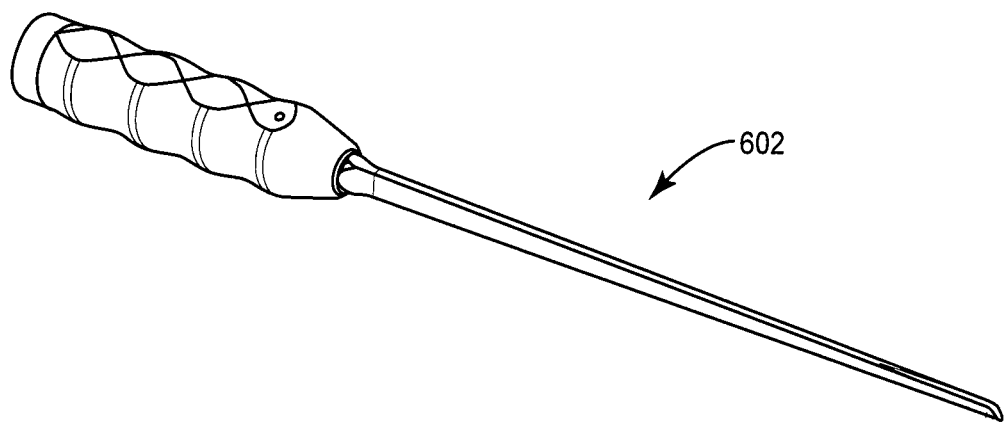
FIG. 15 is a perspective view of components of one embodiment of a system in accordance with the principles of the present disclosure.
Figure 16:
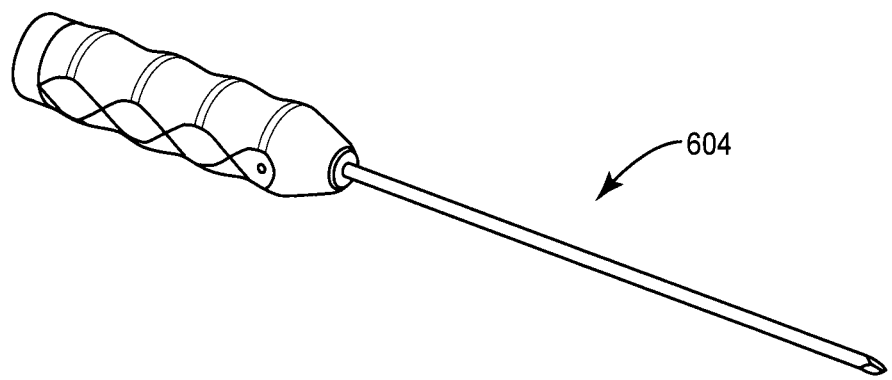
FIG. 16 is a perspective view of components of one embodiment of a system in accordance with the principles of the present disclosure.
Figure 17:
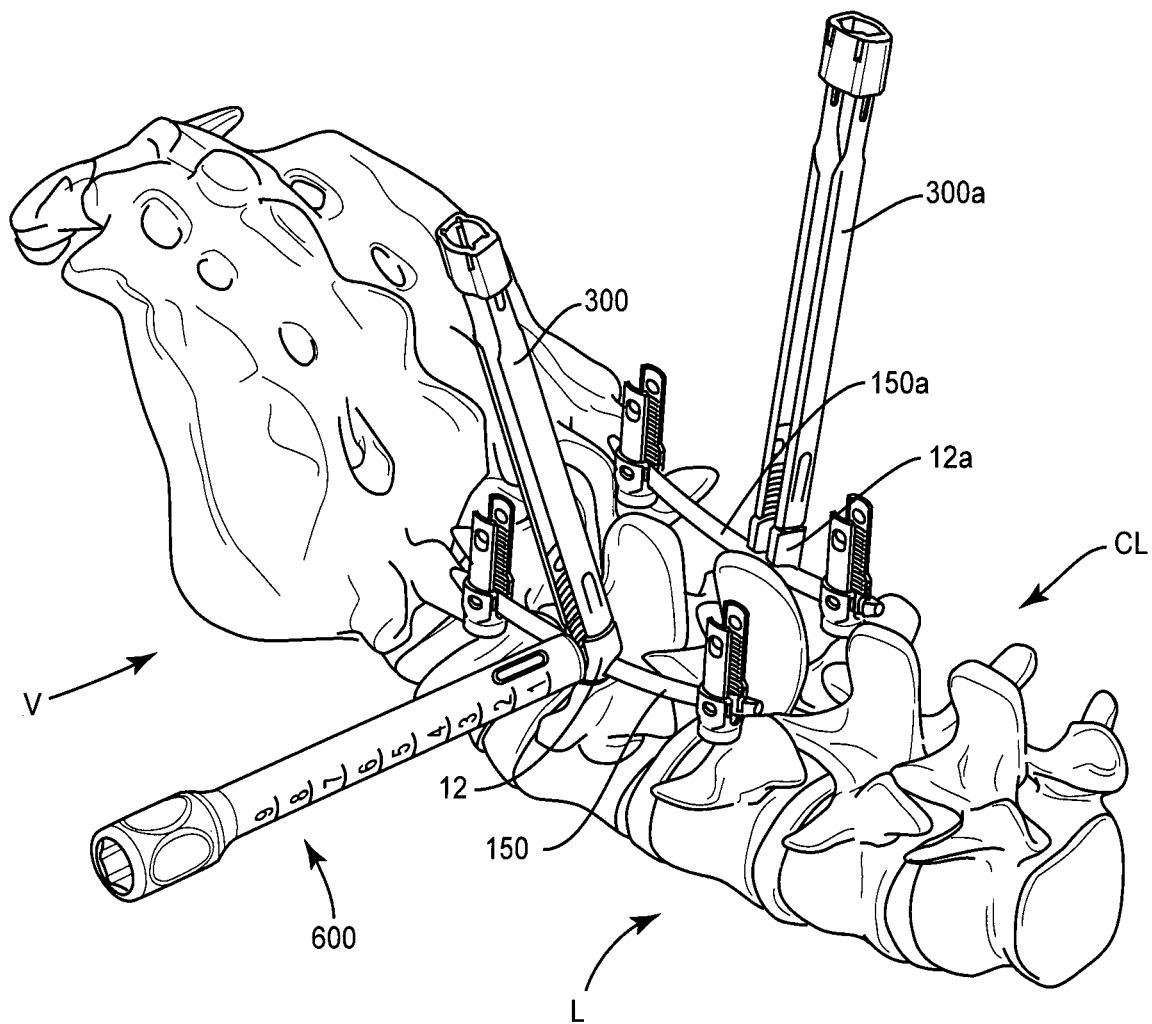
FIG. 17 is a perspective view of components of one embodiment of a system in accordance with the principles of the present disclosure disposed with vertebrae.
Figure 18:
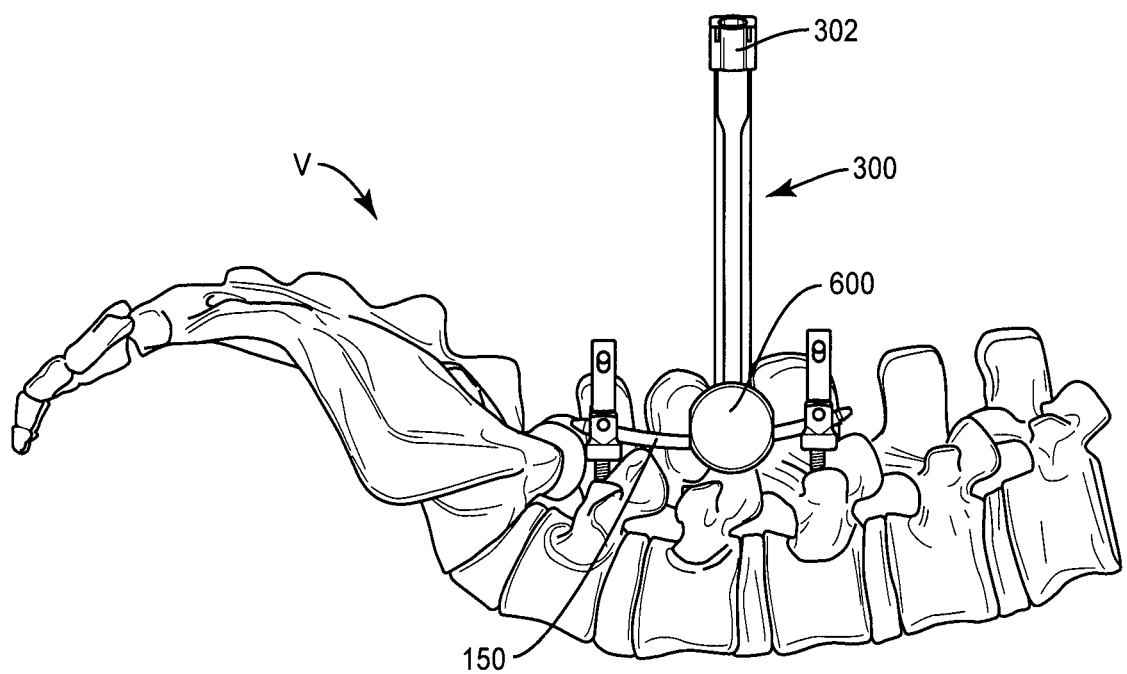
FIG. 18 is a side view of the components and vertebrae shown in FIG. 17.
Figure 19:
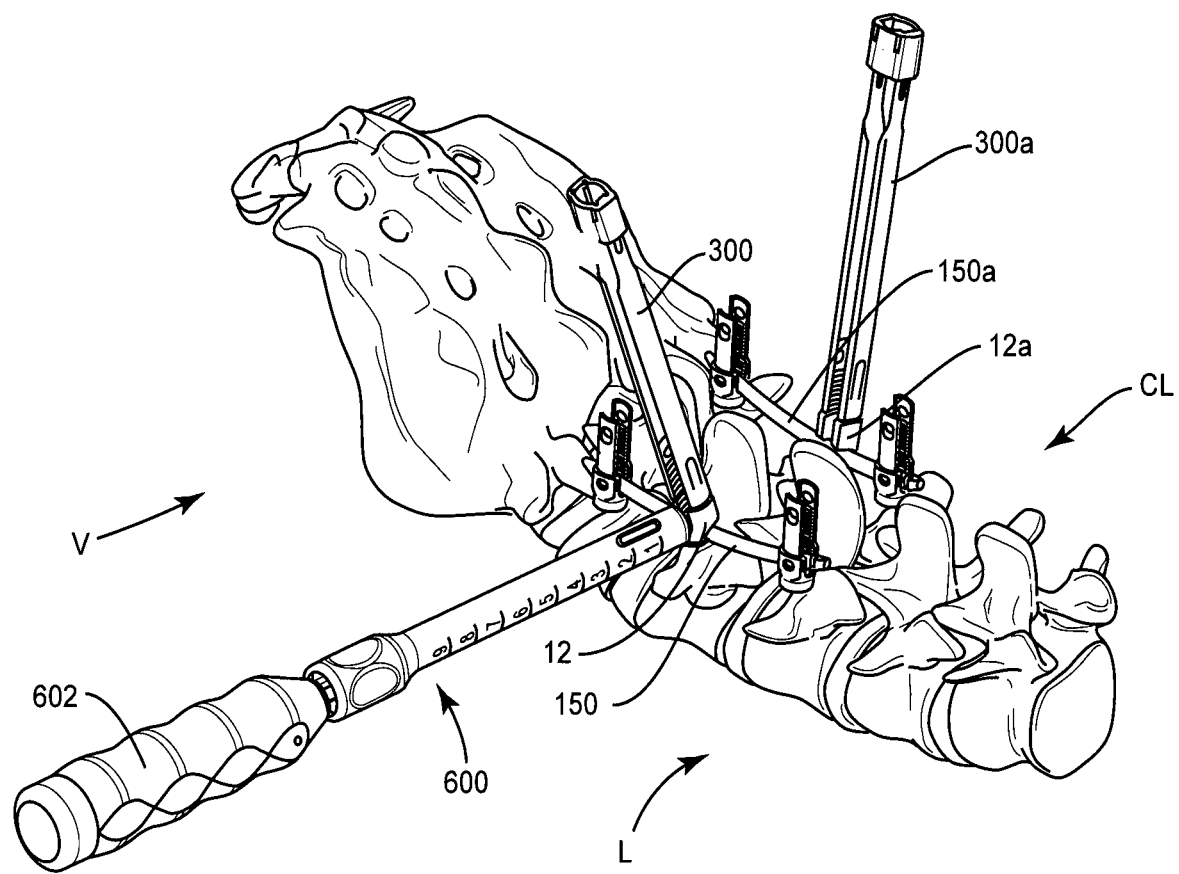
FIG. 19 is a perspective view of components of one embodiment of a system in accordance with the principles of the present disclosure disposed with vertebrae.
Figure 20:
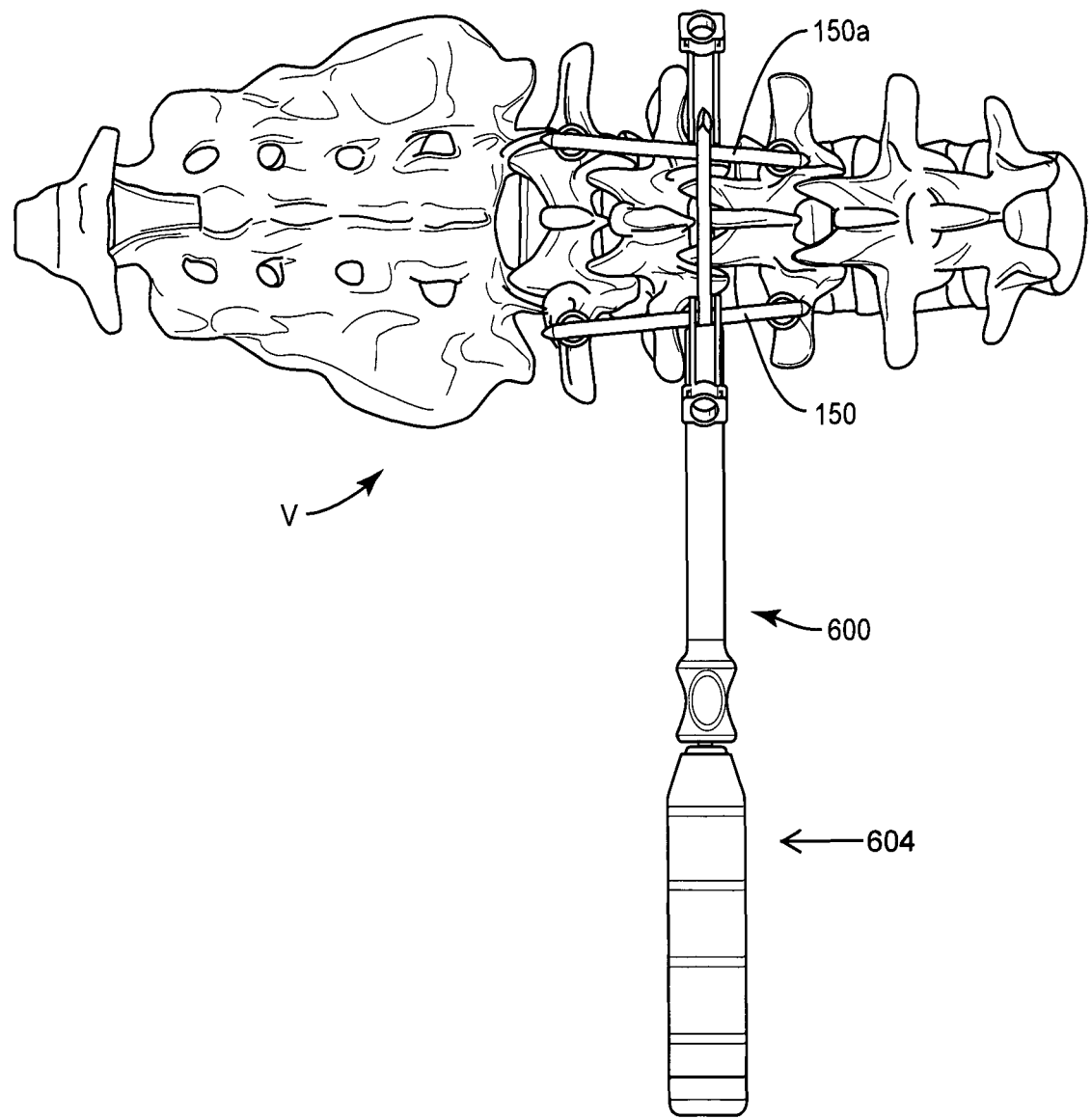
FIG. 20 is a plan view of the components and vertebrae shown in FIG. 19.
Figure 21:
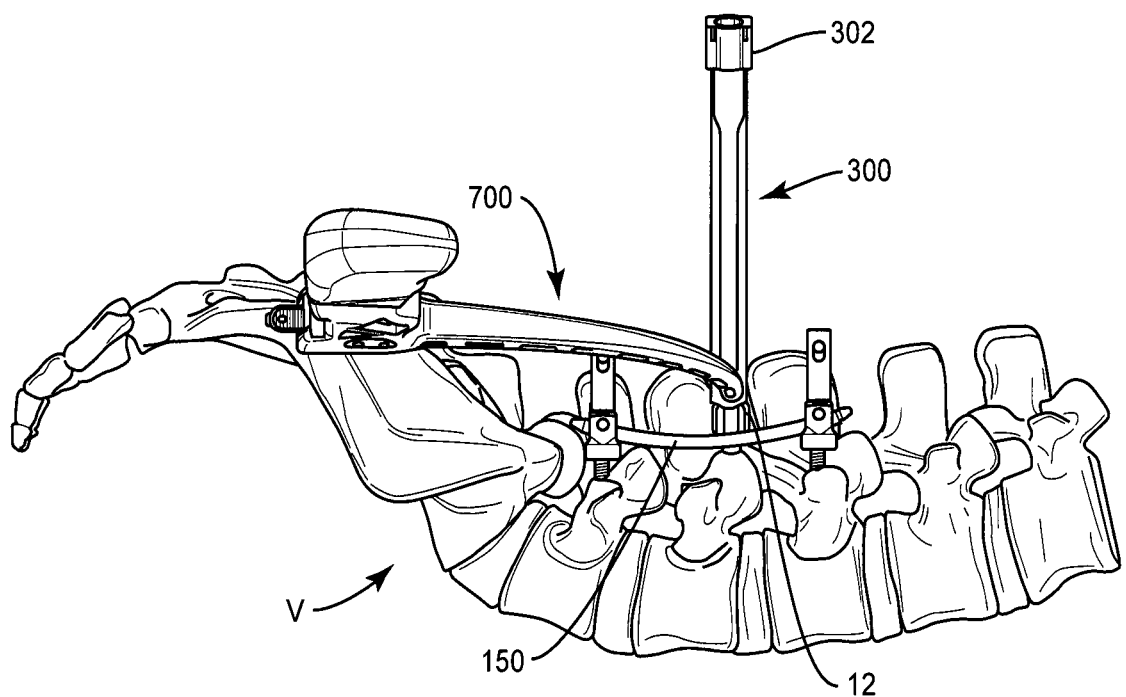
FIG. 21 is a plan view of components of one embodiment of a system in accordance with the principles of the present disclosure disposed with vertebrae.

In some embodiments, a dilator 600 is disposed with vertebrae V though a lateral approach, as shown in FIGS. 17-20. Dilator 600 is configured to provide a passageway for spinal rod 152 for engagement with connectors 12, 12a. In some embodiments, a trocar 602, as shown in FIG. 15, and/or a chisel 604, as shown in FIG. 16, are engaged with dilator 600 to cut and/or disrupt tissue surfaces of vertebrae V for passage of spinal rod 152. In some embodiments, trocar 602 and/or chisel 604 are configured to cut and/or disrupt tissue to clear passageway through tissue, such as, for example, a spinous process and/or a supraspinatus ligament.

Figure 22:
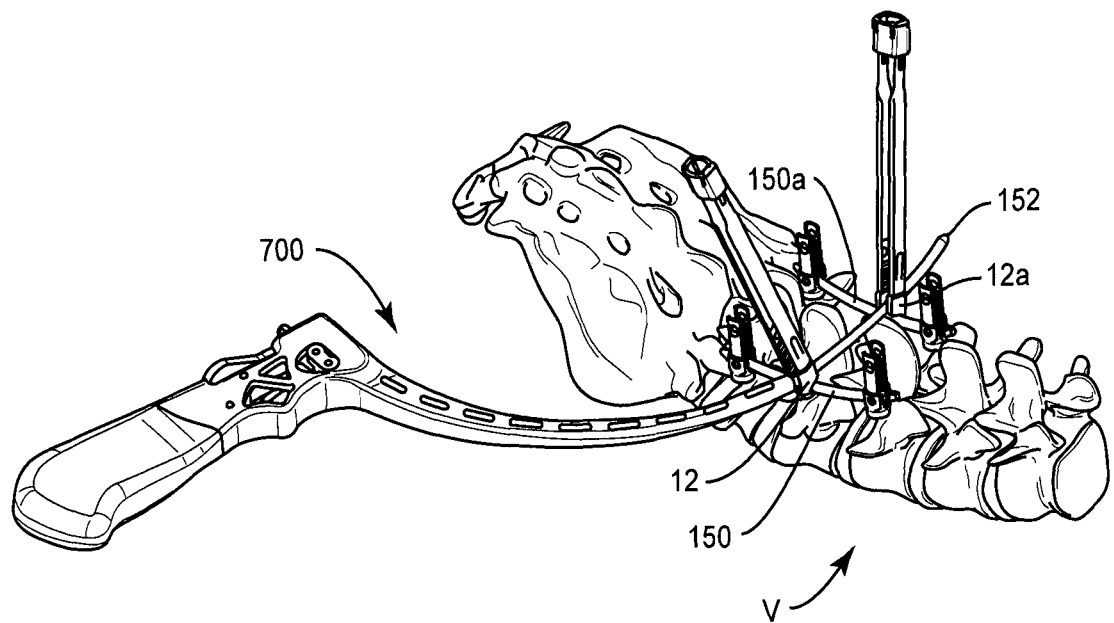
FIG. 22 is a perspective view of the components and vertebrae shown in FIG. 21.
Figure 23:
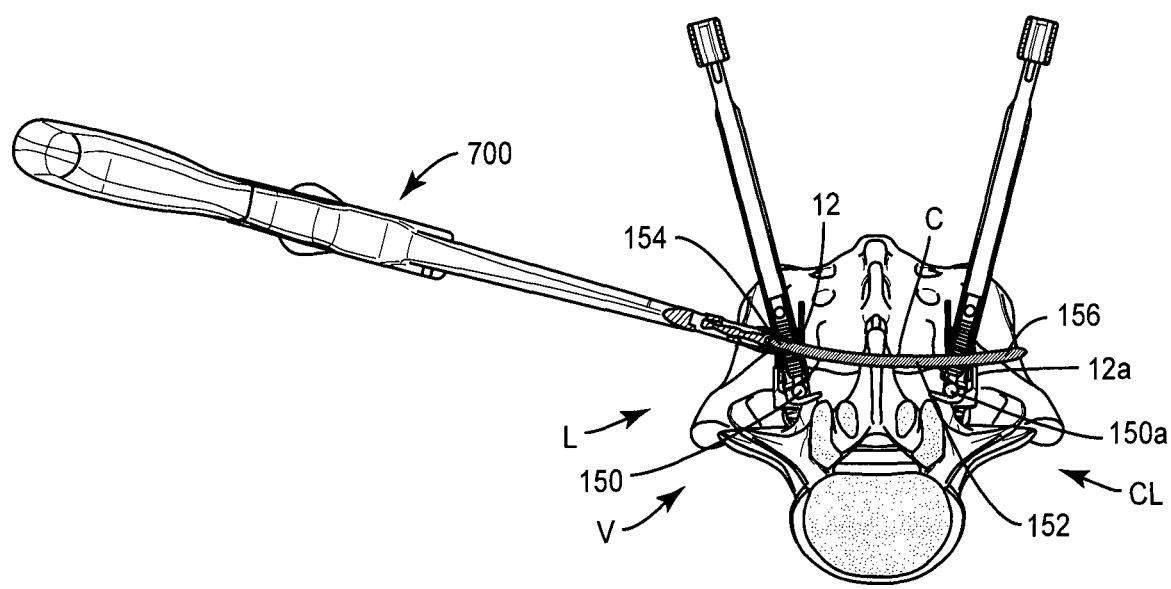
FIG. 23 is a plan view, in part cross section, of the components and vertebrae shown in FIG. 21.
Figure 24:
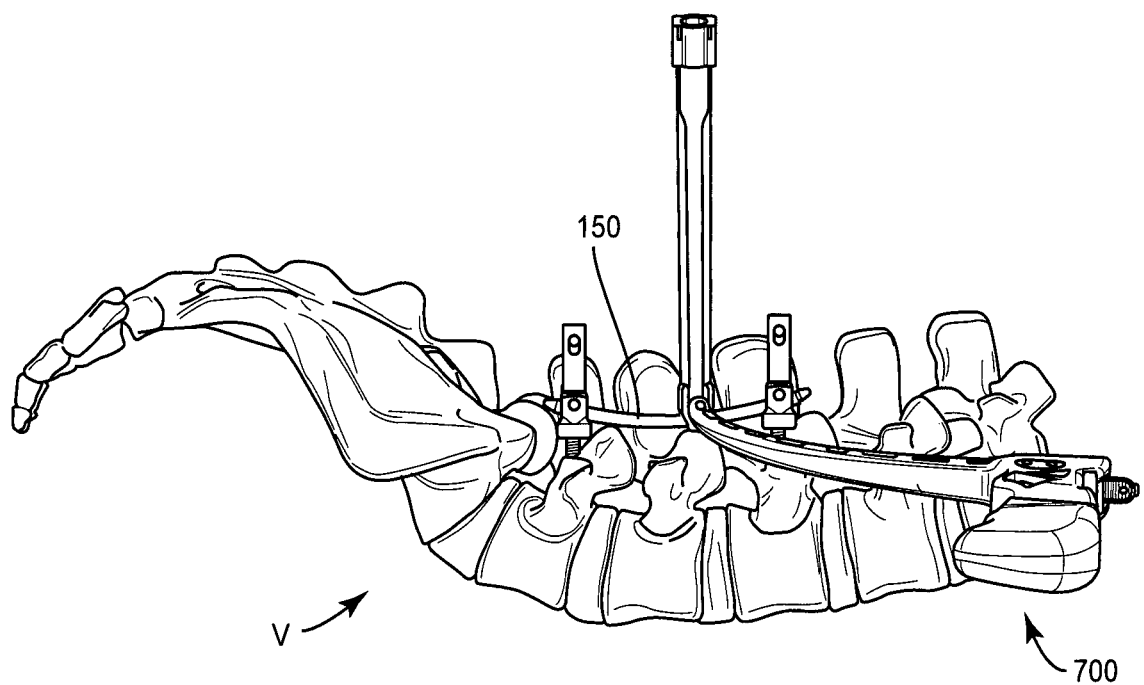
FIG. 24 is a plan view of the components and vertebrae shown in FIG. 21.
Figure 25:
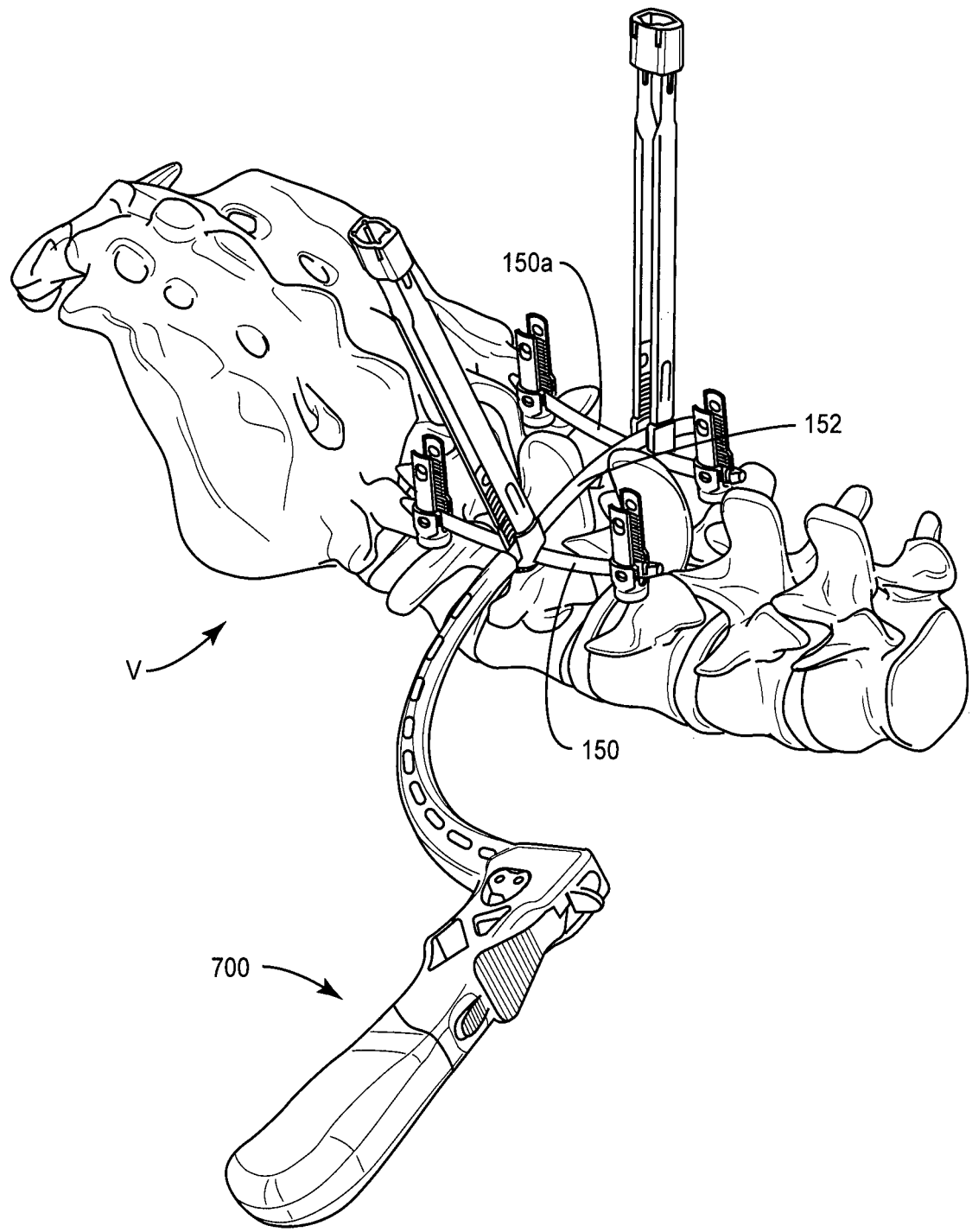
FIG. 25 is a perspective view of the components and vertebrae shown in FIG. 21.
Figure 26:
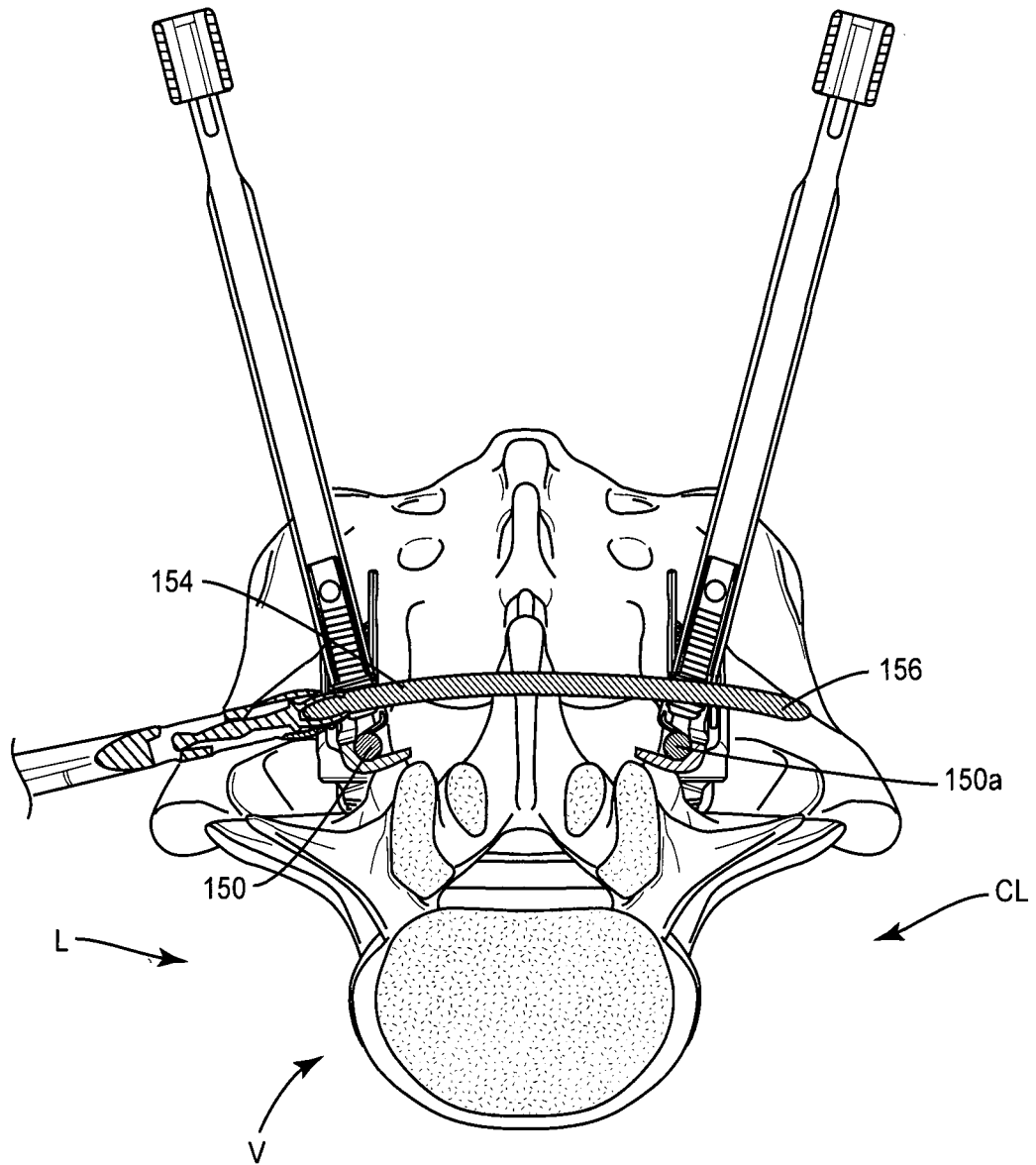
FIG. 26 is a plan view, in part cross section, of the components and vertebrae shown in FIG. 21.

In some embodiments, a rod inserter 700 is engaged with groove 172 of spinal rod 152, as shown in FIGS. 21-26. Rod inserter 700 directs and/or guides spinal rod 152 into cavity 34 of connector 12, laterally across vertebrae V, and into cavity 34a of connector 12a. In some embodiments, a percutaneous endoscopic lumbar discectomy is utilized. End 154 of spinal rod 152 is disposed with cavity 34 and end 156 of spinal rod 152 is disposed with cavity 34a, as shown in FIG. 23. Spinal rod 152 is initially inserted such that an apex of curvature C is oriented towards the spinal canal, as shown in FIGS. 22 and 23. Upon disposal of spinal rod 152 with cavities 34, 34a, rod inserter 700 is rotated, for example, 180 degrees to direct the apex of curvature away from the spinal canal to resist and/or prevent impingement of spinal rod 152 in the spinal canal, as shown in FIGS. 24-26.

Figure 27:
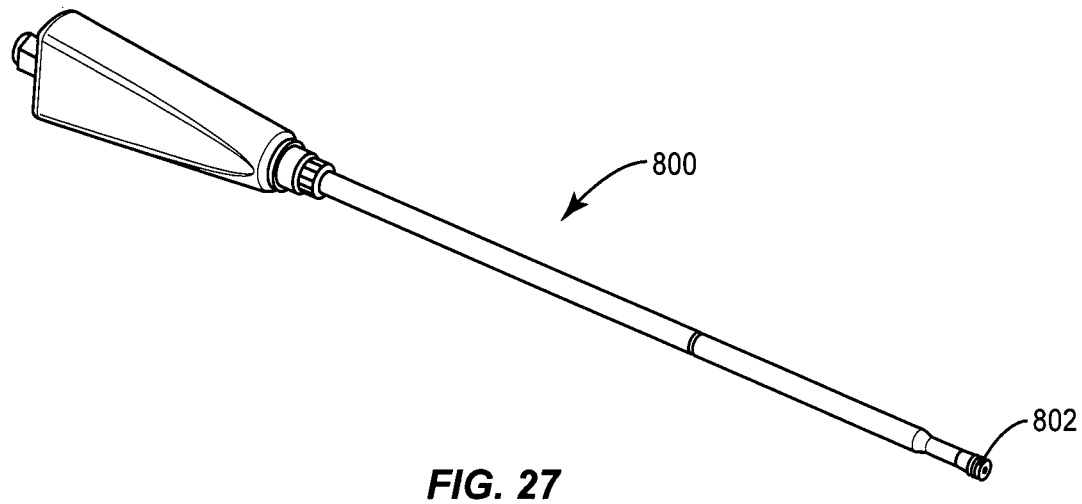
FIG. 27 is a perspective view of components of one embodiment of a system in accordance with the principles of the present disclosure.
Figure 28:
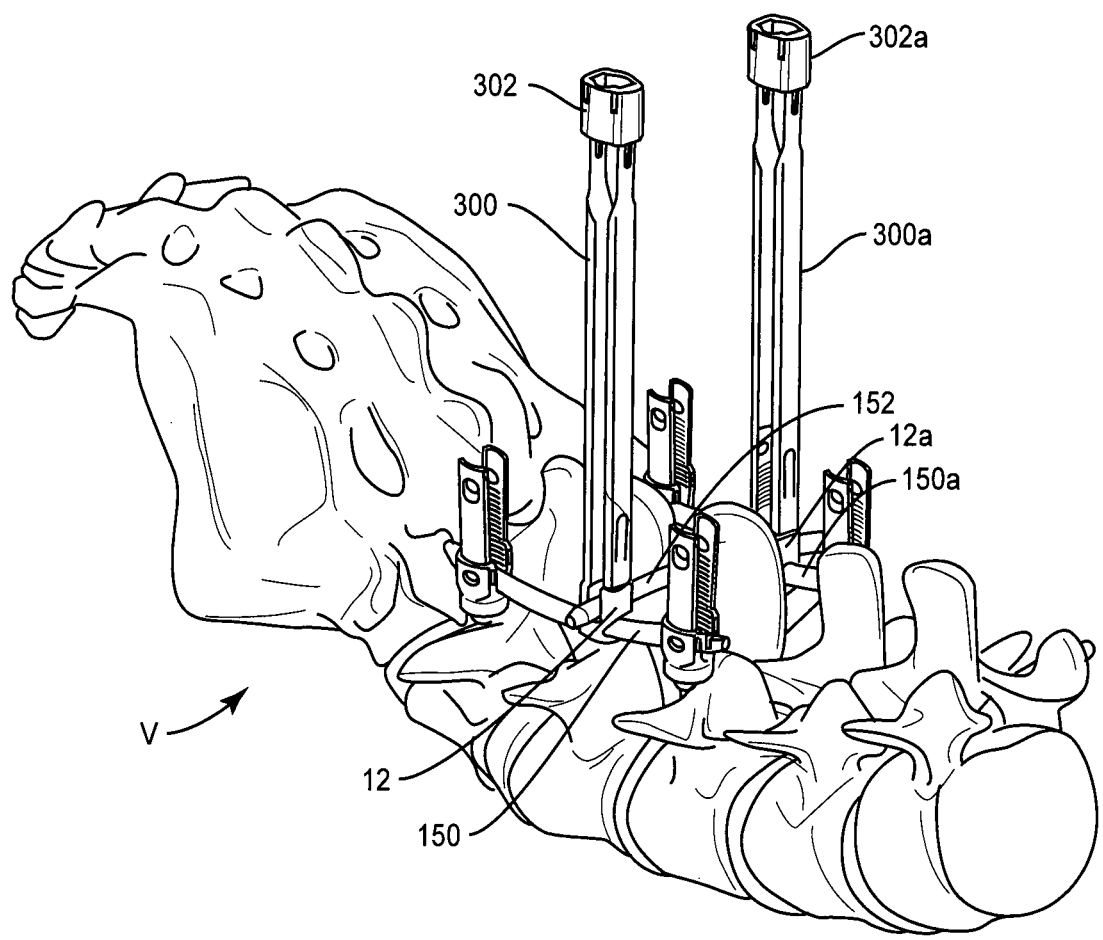
FIG. 28 is a perspective view of components of one embodiment of a system in accordance with the principles of the present disclosure disposed with vertebrae.
Figure 29:
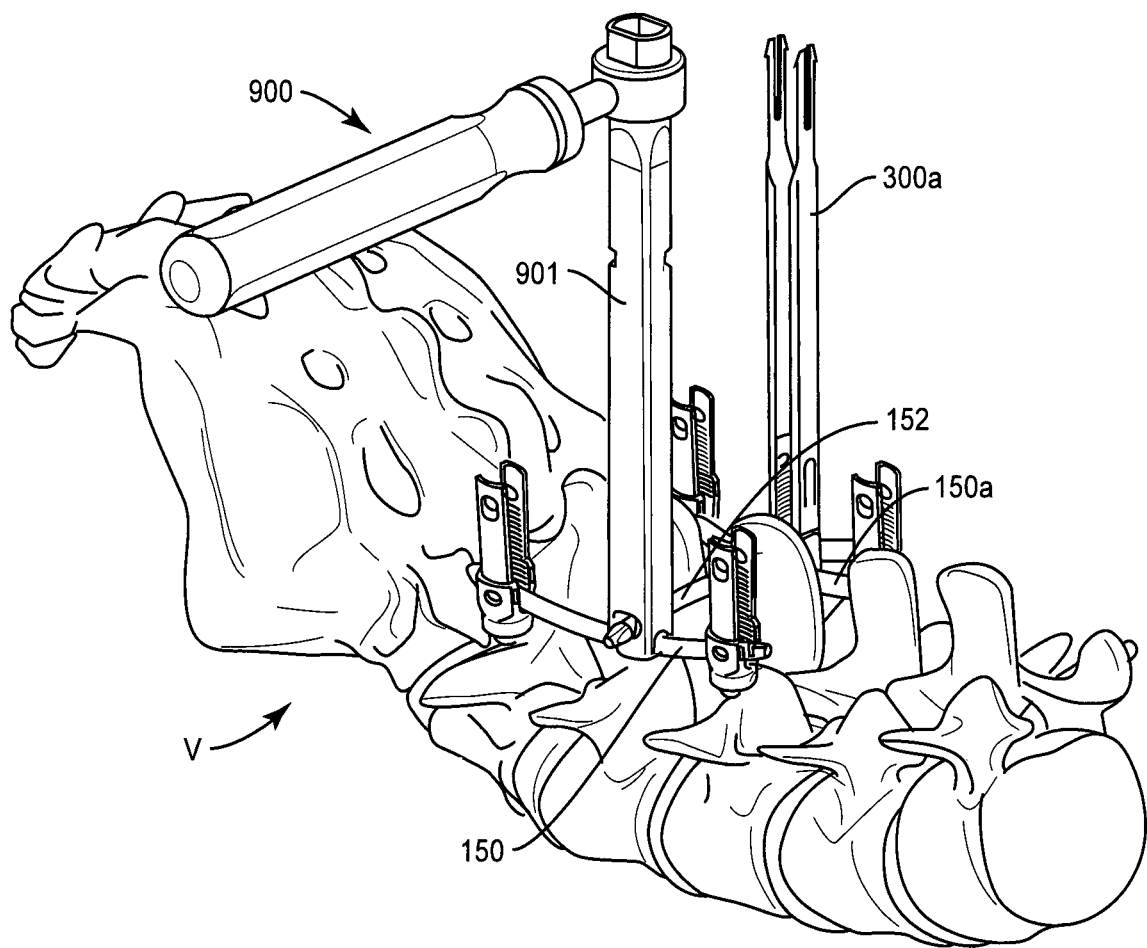
FIG. 29 is a perspective view of components of one embodiment of a system in accordance with the principles of the present disclosure disposed with vertebrae.
Figure 30:
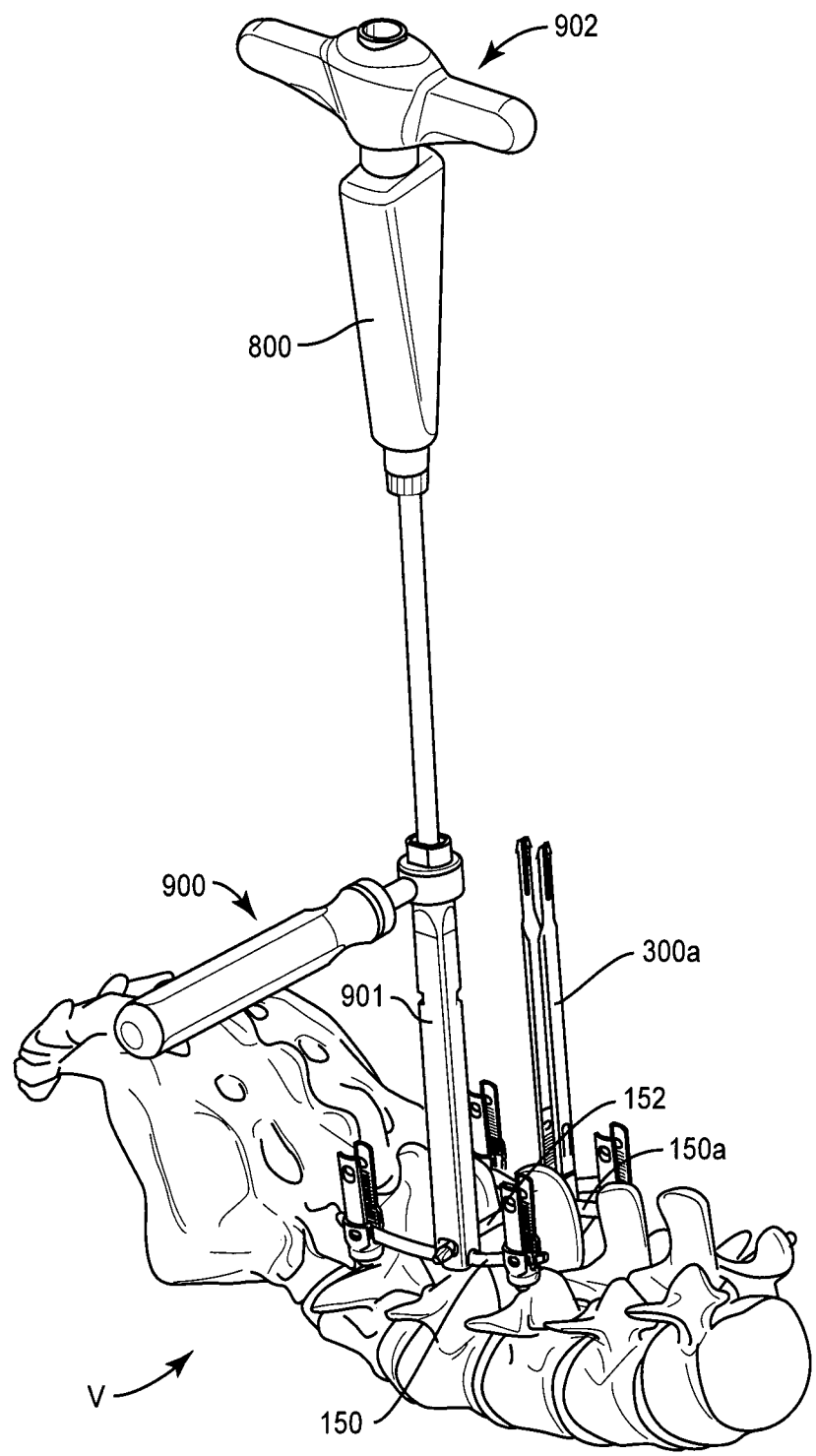
FIG. 30 is a perspective view of components of one embodiment of a system in accordance with the principles of the present disclosure disposed with vertebrae.

In some embodiments, a driver 800 is utilized to engage a set screw 802 with connectors 12, 12a. Driver 802 directs and/or guides set screw 802 through each of extender caps 302, 302a and tab extenders 300, 300a into engagement with connectors 12, 12a. Set screw 802 engages arms 30, 32 and arms 30a, 32a to fix spinal rod 152 within each of cavities 34, 34a, as shown in FIGS. 27 and 28. In some embodiments, a tab hook counter torque handle 900 and a tab hook counter torque sleeve 901 are engaged with tab extenders 300, 300a, as shown in FIG. 29. Handle 900 and sleeve 901 are configured to provide additional leverage to facilitate removing and/or separating a frangible or break off portion of set screw 802 at a selected torque limit. A break off handle 902 is disposed with driver 800 and is manipulated to apply a force to set screw 802 for tightening and the torque limit for break off, as shown in FIG. 30.

Figure 31:
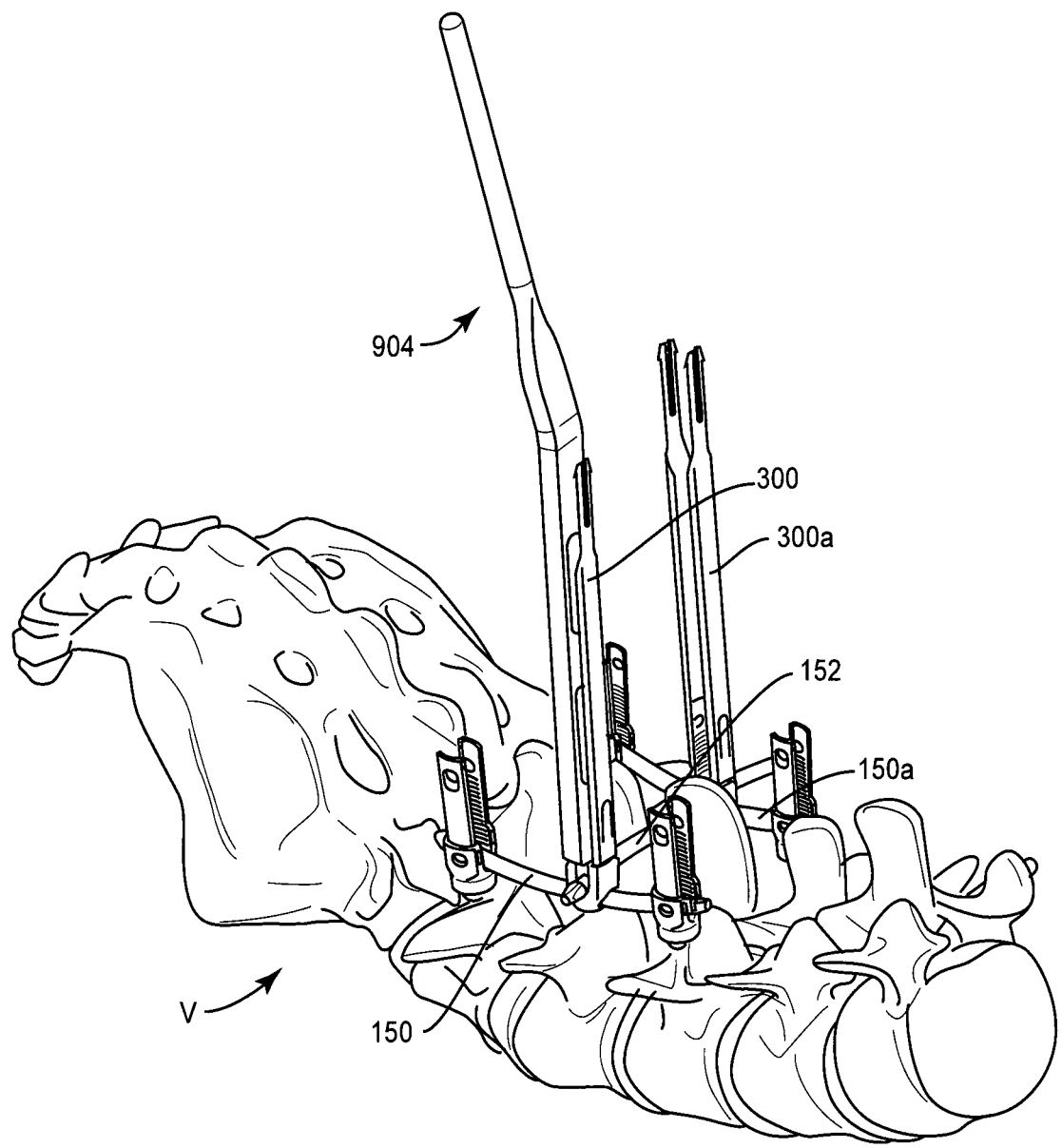
FIG. 31 is a perspective view of components of one embodiment of a system in accordance with the principles of the present disclosure disposed with vertebrae.

Handle 902, sleeve 901 and/or handle 900 are removed from each of extenders 300, 300a. A tab breaker 904 is disposed with each of extenders 300, 300a, as shown in FIG. 31. Tab breaker 904 and is manipulated to apply a force to tabs 44, 54 and tabs 44a, 54a. As the force applied reaches a selected torque limit, tab breaker 902 breaks off tabs 44, 54 and tabs 44a, 54a from connectors 12, 12a, respectively.

In some embodiments, connectors 12, 12a may be employed in a surgical treatment such as a revision surgery to revise, repair and/or extend an existing spinal construct including, for example, bone fasteners 200, 200a, lateral spinal rod 150 and contra-lateral spinal rod 150a, as described herein. In some embodiments, spinal implant system 10 includes connectors 12, 12a employed in a revision surgery to connect with the existing spinal construct. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

Upon completion of the procedure, the surgical instruments, assemblies and non-implanted components of spinal implant system 10 are removed and the incision is closed. Spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In some embodiments, spinal implant system 10 includes one or more fasteners, not shown, for attaching a spinal construct with tissue, as described herein. In some embodiments, the fasteners may be engaged with tissue in various orientations, such as, for example, series, parallel, offset, staggered and/or alternate vertebral levels. In some embodiments, one or more of the fasteners may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A spinal connector comprising:
a body having an upper portion and a lower portion;
a pair of spaced apart arms extending from the upper portion, the arms defining a first implant cavity, the first implant cavity extending along a first axis, the first cavity configured for engagement with a first spinal rod;
a hook extending from the lower portion, the hook having a second cavity configured for engagement with a second spinal rod, the second cavity extending along a second axis, the second axis is transverse to the first axis, wherein the second cavity is in communication with the first cavity and the communication between the first cavity and the second cavity enables the first spinal rod to engage the second spinal rod; and
a provisional spinal rod lock comprising a pair of spaced apart spring tabs configured to engage the second rod, the lock being spaced apart from the hook, the lock being monolithically formed with the upper portion, wherein the second spinal rod directly engages the first spinal rod when the rods are disposed within the respective cavities.

2. The spinal connector of claim 1, wherein the arms include a thread form and further comprising a setscrew configured for engagement with the thread form and the first spinal rod.

3. The spinal connector of claim 2, wherein engagement of the setscrew with the first spinal rod fixes the second spinal rod relative to the body.

4. The spinal connector of claim 1, wherein the lock extends into the second cavity.

5. The spinal connector of claim 1, wherein the spring tabs are each frangibly connected to one of the arms.

6. The spinal connector of claim 1, further comprising the first spinal rod disposed in the first cavity.

7. The spinal connector of claim 1, further comprising the second spinal rod disposed in the second cavity.

8. The spinal connector of claim 1, further comprising the first spinal rod disposed in the first cavity and the second spinal rod disposed in the second cavity.

9. The spinal connector of claim 8, further comprising a ruler configured to measure a distance between the second spinal rod and a third spinal rod.

10. The spinal connector of claim 1, wherein the second cavity defines a horizontal axis, the lock being offset from the horizontal axis.

11. The spinal connector of claim 1, wherein the lock is spaced apart from the first cavity.

12. The spinal connector of claim 1, wherein proximal ends of the arms define an opening that is in communication with the first cavity and configured of top loading a spinal rod into the first cavity.

13. The spinal connector of claim 1, wherein the first implant cavity is positioned between the spring tabs.

14. The spinal connector of claim 1, wherein the body includes a threaded break away tab extending from each of the arms.

15. The spinal connector of claim 1, wherein the body includes a break away tab extender extending from each of the arms, the break away tabs each being frangibly coupled to one of the arms such that threads of each of the break away tabs are continuous with threads of one of the arms.

16. The spinal connector of claim 1, wherein the body includes a threaded break away tab extending from each of the arms, the spinal connector further comprising an extender tab removably connected with each of the break away tabs and an extender cap engaged with the extender tabs.

17. A surgical system comprising:
the spinal connector of claim 1; and
a second spinal connector comprising a pair of spaced apart arms defining a third implant cavity, the third cavity configured for engagement with the first spinal rod, the second spinal connector comprising a second hook extending from a lower portion of the second spinal connector, the second hook having a fourth cavity configured for engagement with a third spinal rod, wherein the fourth cavity in communication with the third cavity and the communication between the third cavity and the fourth cavity enables the first spinal rod to engage the third spinal rod, the second spinal connector comprising a second provisional spinal rod lock comprising a pair of spaced apart spring tabs configured to engage the third rod, the second lock being spaced apart from the second hook, the second lock being monolithically formed with an upper portion of the second spinal connector, wherein the third spinal rod directly engages the first spinal rod when the rods are disposed within the respective cavities.

18. The spinal system of claim 17, further comprising the first rod, the second rod, and the third rod.

19. The spinal system of claim 17, further comprising set screws, each of the set screws threadedly engaged with the one of the upper portions and the first spinal rod.

20. A spinal construct comprising:
a spinal connector having a body having an upper portion and a lower portion, a pair of spaced apart arms extending from the upper portion, the arms defining a first implant cavity and including a thread form, a breakaway tab is frangibly connected to each arm, the first implant cavity extending along a first axis, a hook extending from the lower portion, the hook having a second cavity configured for engagement with a second spinal rod, the second cavity in communication with the first cavity, the second cavity extending along a second axis, the second axis is transverse to the first axis, and a provisional spinal rod lock comprising a pair of spaced apart spring tabs that each extend into the second cavity, the lock being spaced apart from the hook, and the lock is monolithically formed with the upper portion;
a first rod disposed in the first implant cavity;
a second rod disposed in the second implant cavity and engaged with the provisional spinal rod lock, the second rod directly contacting the first rod, wherein the communication between the first cavity and the second cavity enables the first spinal rod to directly contact the second spinal rod; and a setscrew configured for engagement with the thread form and the first spinal rod to fix the first rod and the second rod in the respective first implant cavity and the second implant cavity.

* * * * *